United States Patent [19]

Bressan et al.

[11] Patent Number: 5,801,028
[45] Date of Patent: Sep. 1, 1998

[54] OSMOTIN GENE PROMOTER AND USE THEREOF

[75] Inventors: Ray Bressan; Paul M. Hasegawa, both of W. Lafayette, Ind.

[73] Assignee: Purdue Research Foundation, West Lafayette, Ind.

[21] Appl. No.: 482,037

[22] Filed: Jun. 7, 1995

Related U.S. Application Data

[60] Division of Ser. No. 180,428, Jan. 12, 1994, abandoned, which is a continuation-in-part of Ser. No. 65,147, May 20, 1993.
[51] Int. Cl.$^6$ .................. C12N 15/29; C12N 15/82; A01H 4/00; A01H 5/00
[52] U.S. Cl. .............. 435/172.3; 800/205; 435/320.1; 435/200; 435/419; 536/23.6; 536/24.5
[58] Field of Search .............. 800/205; 435/172.3, 435/240.4, 320.1, 200, 419; 536/24.1, 23.6, 24.5

[56] References Cited

U.S. PATENT DOCUMENTS 4,940,840   7/1990   Suslow et al. .................. 800/205

OTHER PUBLICATIONS

Melchers et al. Extracellular targeting of the vacuolar tobacco proteins AP24, chitinase, and beta–1,3–glucanase in transgenic plants. Plant Molecular Biology 21: 583–593, Feb. 1993.

Bass et al. A maize ribosome–inactivating protein is controlled by the transcriptional activator Opaque-2. The Plant Cell, vol. 4, 225–234, Feb. 1992.

Toubart et al. Cloning an characterization of the gene encoding the endopolygalacturonase–inhibiting protein of *Phaseolus vulgaris* L., Feb. 1992.

Singh et al. Molecular cloning of osmotin and regulation of its expression by ABA and adaptaion to low water potential. Plant Physiol. (1989) 90, 1096–1101, 1989.

*Primary Examiner*—Douglas W. Robinson
*Assistant Examiner*—Thomas Haas
*Attorney, Agent, or Firm*—Woodard, Emhardt, Naughton Moriarty & McNett

[57] ABSTRACT

Described are an isolated DNA fragment incorporating an osmotin gene promoter sequence, recombinant DNA incorporating a foreign structural gene under control of an osmotin gene promoter sequence, as well as methods and transformants involving the isolated DNA fragment and recombinant DNA. Also described are methods for the inhibition of fungal, insect, nematode, and viral pathogens in a plant using such recombinant DNA.

14 Claims, 6 Drawing Sheets

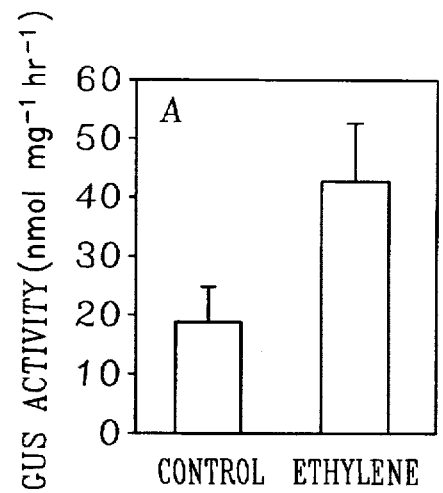
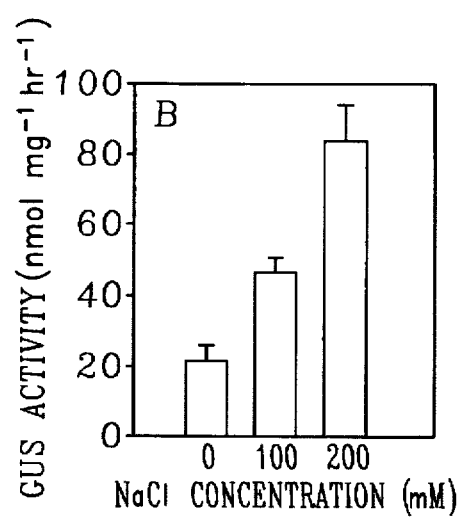
Fig. 4
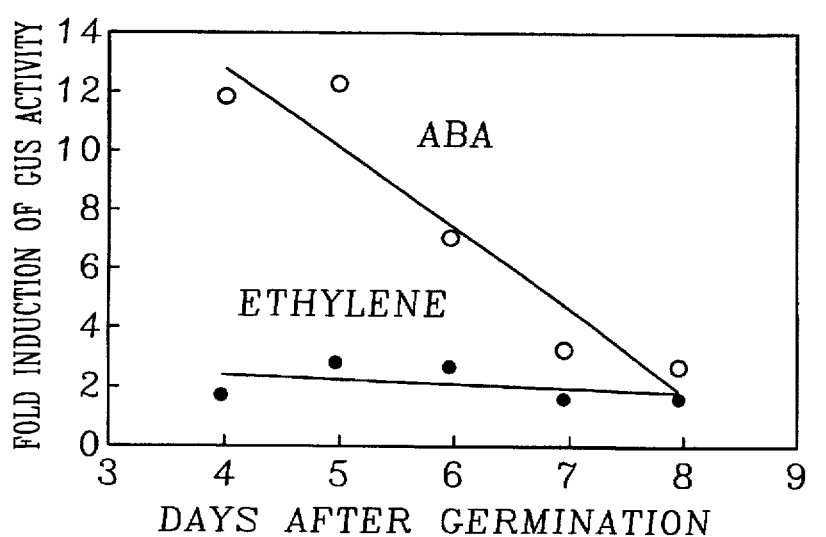
Fig. 5

```
GTCGACTTTGTATCAGTTGATGTTCTGGTAGTATTACACTAGACTTAGTTCGTAACTGATTGTTTATAAATTTCCGGTAACGTCCAAATATGTCCT      -1900
TACCGTCACATAGTTGGTCTATATCCCTTTTGAAATAGAATCCATCCAAATTATTAGCTCTCCGTTAATTATACTAAAATGTATGACAAACACTA      -1800
TTTCCTTTTTATTCAGTACTTTTTTTCTTTATCAATTTAACTGACAAAACTCATGAATTCCTGTAATTTACTATTACAGGCCCCACAGGTTCCTTC      -1700
                                                                   EcoRI
CTGACCTGAAGGAGATGAAAATTATCGGAGAAATTTTTCGGTGGTGTTAATTGGGTGAAGGTAGGATATGATTATTCAAATTTGAAGATCTTGTTCCT    -1600
                                             H-Box                          BglII
TTCAGATCTGAAGCTCCACAGTGAACAACTCCTTCAAAATCTGAATAATTATATCCCTACCGTTCACCCAAATTAACACCACCAAAAAAATTTCTCCGACAAT  -1500
  BglII                                       H-Box
TTTATCTCCCTTTTTCAGAAGAACTAGAGCCTTCTCGGTTGGAAGGTTTGATTTTTAGGAATAAAATCACGTCAAATTGGTAA                   -1400
      TCA
CGAAATGGAGAAGGCACCGAAATGGAGGAAACCGGATATGGGAGAATGAAAAGGGAAAAAAAAGATAAGAAAAGAAAAGAGAAA                 -1300
GGTAAAGAAAAAAAGTACTAATAAAAGTAGATAGTGTTTGTAATACACTTAATACAATTAAAGAAAGAGCTAATTAGTTGGGTGGATTCATTTTAA    -1200
AAAGGGCAACTATGTGACGGTAAGGACATATGTGTATAAGGGCATATATGATGACCAACAATATGTGACGTACGAGTATATATGAGC             -1100
                  as-1
TAAAGTATTAACAAAGGGTAAATGTCTCAATTTGCTATATTACAAAGCCATATTCGACCTTTTCCGTAAATTGGCTAAATTTATGTAGATTTAAAAGCAAC -1000
AACCTATAAGGGGTTGGTCTTTAAATATTGTCTTCATTTTGTCTACTTAAATGTACTACTTAAGAATGAGCTCTGGACCTATATAGTTCTTCAGAGATTTTTCTATTGG -900
   E-8
ATCGCTAGAATTTATGTTATTATTATTCTACTTTTATTGTTAAGTGTTCACAAATTTATTCGATTAGCATGATTTGTGCTAGTTTATTGTTAAACAA    -800
ATTTCACAGAATCGGCGTAACTTTATTTATCTGCAATCGATGTACTTCTTAAATTGTTCATTAAATCTACCTGACTGGTATAATTTTTCTGTGTCTTC   -700
                                    ClaI    TCA
TCTGCGCTATTCTACATCCAGAATAACGATATCTAATTAATGAGCTGCTATATAAATCGATGTAAATCGATTCTCAAAAAGAAAATGAAGGAAGAAAAAC  -600
                              ClaI
TATGTGGTGGGACAATAACATCATCTATATAAAAATTAAAGTGAAATCCAGGATTTCAGTAGTATTAAAACTACAGGAGAAATTATGATCCGTGCAAA    -500
    EcoRV                                                          as-1  ABRE
CTCCATAAAAATTTCGGAAGTAGTACAAAATGTGGAGTCAAACTGATAAATAACGAAACTCTAATAATTTCTTATAATTTTTTATATTTTTGTGACGAATATT -400
                                                                          as-1
ATTGTTTGAGTTTATTTCACATTAAAAACTAAATATTGAATAATAGCTTAAAATGATGGCTATCTGCCAAAAAGTGGCTATCTGTCAATTCTTGCGAAT   -300
TAAAAAAATGGTAGTAAAATAAAAGAAAGCAAGAGAAAATTGACTAAAAAGATATTGTTACAAGTGTCACGTTACGGTTATTACCAAAT            -200
                                                               G-Box
AAATTGACTTCTATATTCATAAAATAATTAATTATTAGGCGGCCTCTATGTGTTAAGGCCGCGGCCCCGCCGCCCCATCTTTGCCAAAGCATCCTTGAGATATCCGTT  -100
  CAAT                                                                      TATA
CAACCCAACTTGTTAAAAAATGTCCAACAatgggcaacttgagatct                                                        0
                                                BglII
                                    100
```

*Fig. 6* ns to
isolated DNA including an osmotin gene promoter, and
recombinant DNA including a foreign gene under control of
the osmotin gene promoter, and transformants including the
recombinant DNA.

Osmotin and osmotin-like proteins (hereinafter
"osmotins") and coding sequences for osmotin proteins have
been studied extensively. Osmotins are a group of cationic
proteins existing in at least two forms, one with a pI>7.8 and
another with a pI>8.2.

Osmotins have been classified as members of the PR-5-
type proteins of tobacco. Studies have shown that the
synthesis and accumulation of osmotin mRNA are develop-
mentally regulated and controlled by at least six hormonal or
environmental signals, including abscisic acid (ABA),
ethylene, tobacco mosaic virus invention, salinity,
desiccation, and wounding in both cultured cells and whole
plants of tobacco. For additional background information
with respect to osmotins, reference can be made to the
following publications: Singh et al., *Plant Physiol.*, 85,
529–536 (1987); Singh et al., *Plant Physiol.*, 90, 1096–1101
(1989); Singh et al., *In NATO ASI Series*, G19, pp. 67–87
"Environmental Stress in Plants", J. H. Cherry, ed (1989);
LaRosa et al., *Plant Physiol.*, 91, 855–861 (1989); Meeks-
Wagner et al., *Plant Cell*, 1, 25–35 (1989); Grosset et al.,
*Plant Physiol.*, 92, 520–527 (1990); Neale et al., *Plant Cell*,
2, 673–684 (1990); Roberts et al., *J. Gen. Microbiol.*, 136,
1771–1778 (1990); Stintzi et al., *Physiol. Mol. Plant
Pathol.*, 38, 137–146 (1991); Woloshuk et al., *Plant Cell*, 3,
619–628 (1991); Singh et al., *Plant Physiol.* 79, 126–137
(1985); Richardson et al., *Nature*, 327, 432–434 (1987); Bol,
*In Temporal and Spatial Regulation of Plant Genes*, D. P. S.
Verma and R. B. Goldberg eds (New York: Springer-Verlag)
pp. 201–221 (1988); Brederode et al., *Mol. Biol.*, 17,
1117–1125 (1991); Linthorst, *Crit. Rev. Plant Sci.*, 10,
123–150 (1991); LaRosa et al., *Plant Physiol.*, 79, 138–142
(1985); La Rosa et al., *Plant Physiol.*, 85, 174–185 (1987);
Singh et al., *Proc. Natl. Acad. Sci. USA*, 84, 739–743.

Despite considerable study of the coding sequences for
osmotins, the prior art has not provided identification of or
characterized promoters for osmotin genes or explored
potential uses of such promoters. This is despite the con-
tinuing need for additional promoters which are useful in
genetic engineering techniques and which may provide
highly advantageous temporal and/or spatial expression of
genes. Such regulation of expression-allows for great vari-
ability in the manner in which the promoter is used including
the capacity to express gene products in response to par-
ticular applied environmental signals, or to express gene
products in specific tissues or developmental stages in which
the expression is maximally beneficial.

It has been discovered that regulation of osmotin protein
expression in plants is controlled by the osmotin promoter.
Fusion of the osmotin promoter to a heterologous gene
results in unique temporal and spatial expression of the
heterologous gene in transformed plants. The osmotin pro-
moter is therefore a transcription regulatory element which
can be used to control the expression of operably linked
genes under unique conditions and in targeted tissues and
developmental stages of transformed plants.

SUMMARY OF THE INVENTION

The present invention is based upon the isolation and
characterization of an osmotin promoter and discovery that
osmotin promoters can be fused with foreign genes to result
in recombinant DNA having the genes under control of the
osmotin promoter and useful to transform host cells so as to
enable advantageous expression of the gene. In this regard,
advantageously, the invention provides promoters that can
be used to achieve expression of gene products in response
to externally-applied signals (i.e. induced expression) as
well as in specific tissues and developmental stages of
transformed plants. Accordingly, one preferred embodiment
of the invention provides an isolated DNA fragment includ-
ing an osmotin gene promoter sequence. This isolated frag-
ment is preferably free from the complete osmotin coding
sequence but may contain a portion of the gene, say, no
greater than about 100 base pairs of the gene, or may be free
from any portion of the coding sequence.

Another preferred embodiment of the invention provides
recombinant DNA including a foreign gene under control of
an osmotin gene promoter sequence.

Another preferred embodiment of the invention provides
a host cell which includes recombinant DNA comprising a
foreign gene under control of an osmotin gene promoter
sequence so as to enable expression of the gene in the host
cell.

Another preferred embodiment of the invention provides
a plant transformant including recombinant DNA which
comprises a foreign gene under control of an osmotin
promoter sequence so as to enable expression of the gene in
the plant transformant. The transformant can be, for
example, one which exhibits tissue specific expression of the
foreign gene under the control of the osmotin gene promoter,
and/or which expresses the gene in response to applied
external signals such as hormones, wounding, or conditions
of desiccation.

Another preferred embodiment of the invention provides
a method for achieving expression of a gene in a host cell,
comprising the step of fusing the gene with a DNA fragment
containing an osmotin promoter sequence so as to form
recombinant DNA having the gene under control of the
osmotin promoter sequence. This process further includes
the steps of transforming a host cell with the recombinant
DNA, and culturing the cell under conditions to achieve
expression of the gene.

Additional preferred embodiments, features and advan-
tages of the invention will be apparent from the description
which follows.

BRIEF DESCRIPTION OF THE FIGURES

FIG. 4 shows GUS activity of transformants of the invention as induced by ethylene (A) (5 mg/l for 24 hours) and NaCl (B) (24 hour treatment with indicated concentrations).

FIG. 5 shows fold induction of GUS activity by ABA (100 mm, 24 hours) and ethylene (5 mg/l, 24 hours) in the early growth stage of transformed seedlings of the invention.

FIG. 6 shows the nucleotide sequence of the osmotin promoter and various cis regulatory elements. The sequences corresponding to ABRE, as-1, GT-1, GT-2, E-8, TCA and H-box are indicated in the figure. An inverted repeat sequence of 82 bp present at the 5' end of the promoter is underlined. The underlined region between the restriction sites ClaI and EcoRV represents the sequence protected by nuclear proteins from DNaseI digestion. Two possible translation start sites (ATG) are also indicated in the figure.

DESCRIPTION OF THE PREFERRED EMBODIMENT

Figure 1:
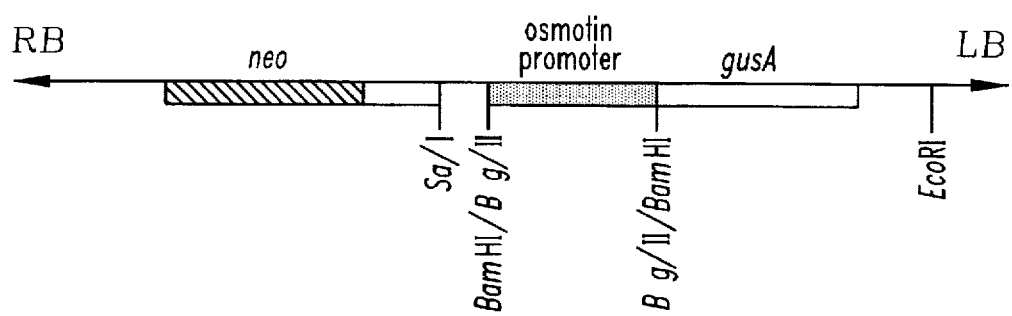
FIG. 1 illustrates features of the recombinant DNA mol-
ecule employed in the transformations described in the
Examples. RB=right border; LB=left border; neo=
Neomycin phosphotransferase II gene; gusA=GUS reporter
gene.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention pertains.

It has been discovered that distinct aspects of osmotin expression in plants are effected at the level of transcriptional activation by the promoter associated with the given osmotin gene ("an osmotin promoter"). Fusing a heterologous gene under the transcriptional control of an osmotin promoter within the present invention results in unique temporal and spatial expression of the heterologous gene in transformed plants. Thus, an osmotin promoter can be used to control the expression in transformed plants of operably linked genes under conditions and in targeted tissues which are characteristic of osmotin expression.

The present invention is useful inter alia for genetically modifying cells, tissues, or organisms in which the osmotin promoter is operable for achieving expression of a foreign structural gene of interest. These include for example eukaryotic cells such as plant cells, eukaryotic tissues such as plant tissues, and whole plants. The genetic modification can include for instance inserting foreign useful structural genes from other species, organisms, or strains. Representative useful foreign structural genes include genes conveying identifiable phenotypes such as improved tolerance to extremes of heat or cold; improved tolerance to anaerobic conditions (e.g. water-logging), drought, or osmotic stress; improved resistance or tolerance to pests such as insects (e.g. insecticidal toxins such as the *Bacillus thuringiensis* crystal protein), arachnids, nematodes, or epiphyte pests and fungal, bacterial, or viral diseases; the production of enzymes or secondary metabolites not normally found in the cells, tissues or organisms; improved nutritional (e.g. lectins and storage proteins such as zein or phaseolin), flavor (e.g. sweet proteins such as thaumatin), or processing properties when used for fiber or human or animal food; changed morphological traits or developmental patterns (for instance leaf hairs which protect the plant from insects, coloring which is aesthetically pleasing, changed plant growth habits, dwarf plants, reduced time needed for the plants to reach maturity, expression of a gene in a tissue or at a time that gene is not usually expressed, and the like); male sterility; improved photosynthetic efficiency (including lowered photorespiration); improved nitrogen fixation; improved uptake of nutrients; improved tolerance to herbicides (e.g. glyphosate or triazines); increased crop yield; improved competition with other plants; genetic markers novel to the genetically modified material; and the like. Genetic markers can be used to improve germplasm identification by the presence of one or more characteristic nucleic acid sequences, proteins, gene products, or phenotypes however identified. Genetic markers can distinguish a genetically modified plant or plant cell of the present invention from plants or plant cells which are not so modified, to facilitate transfer of a genetically linked or cotransformed artificially introduced DNA sequence or phenotype by other (e.g. sexual) means to other genotypes, or to facilitate identification of plants protected by patents or by plant variety protection certificates. Resistance (or tolerance) in cell or tissue culture to selective agents (i.e. selectable markers) and markers that are readily identified during screening (e.g. screenable markers such as distinctive cell-surface antigens or enzymes, like β-galactoxidase, that are readily recognized visually) are also useful genetic markers. The invention is exemplified by placing a structural gene encoding β-glucuronidase (GUS) and providing an identifiable phenotype under the control of a promoter region which in nature controls expression of osmotin. The promoter/GUS combination can be used to detect and select cells transformed by the combination. Cells transformed by linked DNA sequences may therefore be identified, as will be understood by those in the art. Other uses of the invention, exploiting the properties of other structural genes introduced into various plant species, will be readily apparent to those skilled in the art.

As used herein the term foreign structural gene includes that portion of a gene comprising a DNA segment which encodes a foreign RNA, protein, polypeptide, or portion thereof, possibly also including a translational start codon. A foreign structural gene may encode a gene product not normally found in the cell in which the gene is introduced. Additionally, the term refers to copies of a structural gene naturally found within the cell which are introduced artificially. A foreign structural gene may be partially or completely derived from prokaryotic DNA, eukaryotic DNA, episomal DNA, plasmid DNA, genomic DNA, cDNA, viral DNA, viral cDNA, chemically synthesized DNA, or the like. A foreign structural gene may contain one or more modifications in the coding segments and/or untranslated regions which may affect the biological activity or chemical structure of the expression product, the rate of expression or the manner of expression control. Representative modifications include mutations, insertions, deletions, and substitutions of one or more nucleotides. "Silent" modifications that do not alter the chemical structure of the expression product but which affect intercellular localization, transport, excretion or stability of the expression product may also be present in the foreign structural gene. The structural gene may be an uninterrupted coding sequence or may include one or more introns, bounded by the appropriate functional splice junctions, which may be obtained from a synthetic or naturally occurring source. The structural gene may be a composite of segments derived from a plurality of sources, naturally occurring or synthetic coding for a composite protein, the composite protein being foreign to the cell into which the gene is introduced and expressed or being derived in part from a foreign protein. The foreign structural gene may be a fusion protein, and in particular, may be fused to all or part of a structural gene served from that which the transcriptional control sequences were derived.

In accordance with the invention the foreign structural gene is incorporated in a recombinant DNA molecule (e.g. a plasmid or linear DNA) under control of an osmotin gene promoter. In this regard, a recombinant DNA molecule is one which has been either naturally or artificially produced from parts derived from heterologous sources, which parts may be naturally occurring or chemically synthesized molecules, and wherein those parts have been joined by ligation or other means known to the art. The foreign gene will be under control of the osmotin promoter sequence and thus the gene will be generally downstream from the promoter sequence and, stated alternatively, the promoter sequence will be generally upstream (i.e. at the 5' end) of the gene. In this vein, it is well known that there may or may not be other regulatory elements (e.g. enhancer sequences) needed along with the promoter and a transcriptional start codon to achieve expression of the foreign structural gene. The phrase "under control of" contemplates the presence of such other elements as are necessary to achieve expression of the foreign gene.

Expression refers to the transcription and translation of a structural gene so that a protein is made. Gene expression can be assessed by direct detection of protein product, by protein gel-electrophoresis or immunological methods, and the like. Expression is commonly assessed by detection of the mRNA products of transcription. This method is particularly appropriate for the assessment of transcriptional control factors, such as transcriptional activating elements, since the effects of non-transcriptional factors, such as protein degradation are excluded.

An osmotin gene promoter according to the instant invention is the nucleotide sequence that controls transcriptional activation of an osmotin gene. Among the family of such osmotin promoters contemplated by the present invention is the *Nicotiana* tabacum osmotin promoter discussed in greater detail below. Other members of the osmotin promoter family can be isolated by means of nucleic acid hybridization, using as hybridization probes the nucleotide sequences disclosed herein or portions thereof. Such probes may consist of the entire osmotin gene or portions thereof, including the identified promoter. Alternatively, antibodies to an osmotin protein can be used to screen a plant cDNA library for clones that express the osmotin. The cDNA thus identified as osmotin-encoding can then be used to isolate a genomic clone containing at least a substantial portion of the osmotin gene, from which clone the promoter can be subcloned.

It will be understood that the osmotin gene promoter can be from any suitable source, natural of synthetic. Representative sources include plants that express an osmotin gene, for example sources including but not limited to tobacco, tomato, millet, soybean, carrot, cotton, potato, and alfalfa. As indicated above, advantageous promoter sequences can be obtained from the tobacco plant, *Nicotiana tabacum*, for example the DNA segment between $-1630$ and $+45$ shown in Table 1 below and active fragements of that segment. Advantageous promoters include nucleotides 5' of the osmotin gene extending at least to nucleotide $-248$, with a promoter including nucleotides 5' of the osmotin gene extending to $-1052$ providing very high GUS activity and thus being particularly preferred.

Osmotin gene promoters can typically include, in addition to an RNA polymerase recognition site, cis-acting regulatory elements for transcriptional activation by ABA, ethylene and/or NaCl, and/or repressor elements. It has been discovered that a number of factors activate transcription of the osmotin promoter including ABA, ethylene, NaCl and wounding. Factors that activate the osmotin promoter may vary, depending upon the plant species from which the osmotin gene is isolated. For example, the *N. tabacum* osmotin gene promoter exemplified below has high activity in pericarp tissue at the final desiccating stages of fruit development. The *N. tabacum* osmotin gene promoter also is active in mature pollen grains during anther dehiscence.

An osmotin promoter of the present invention can be employed in controlling the expression of operably linked genes under unique conditions and in targeted tissues of transformed plants. For example, an osmotin promoter can be used to direct the expression of antifungal compounds at the site of the fungal infection. More specifically, fore example, Aspergillus infects desiccating seeds and nuts of peanuts, cereals, cotton and other plants, resulting in the production of aflatoxin. Since an osmotin promoter of the instant invention has high activity in the pericarp tissue as the fruit desiccates, antifungal compounds expressed under the control of the osmotin promoter can be directed to an important site of Aspergillus infection under conditions when infection is most likely.

Since chitinase degrades the chitin that is an integral part of the cell walls of fungi, the chitinase gene is one example of a foreign structural gene that is useful for the present invention. DNA molecules containing chitinase-encoding sequences may be obtained, for example, from ATCC #39637 and ATCC #67152. The chitinase DNA molecules can be used to construct recombinant DNA "vectors," comprising the chitinase gene operably linked to a promoter that is capable of driving the expression of the chitinase gene. For example, see Suslow et al., U.S. Pat. No. 4,940,840. Specifically, the present invention encompasses vectors comprising the osmotin promoter operably linked to a chitinase gene. Preferably, the osmotin promoter in such vectors contains nucleotides 5' of the osmotin gene extending at least to nucleotide $-248$. More preferably, the osmotin promoter in such vectors contains nucleotides 5' of the osmotin gene extending to nucleotide $-1052$. Such vectors can be constructed by replacing the GUS-encoding sequences with chitinase-encoding sequences in the pBI101.1 or pBI201 derivatives, described below. These vectors are suitable for transformation of plants using Agrobacterium or a microprojectile delivery system, as shown herein. Other vectors suitable for plant transformation may be found in Gruber et al., *Methods in Plant Molecular Biology and Biotechnology*, (Glick et al., Eds.), CRC Press, Ann Arbor, MI, pp. 89–119 (1993).

Alternative antifungal compounds include (1-3)-β-glucanase (which degrades a major polysaccharide of fungal cell walls) and ribosome-inactivating protein (which inactivates fungal ribosomes). Full-length cDNAs of glucanase and ribosome-inactivating protein are disclosed in Leah et al., *J. Biol. Chem.* 266, 1564–1573 (1991). In addition, Logemann et al., *Bio/Technology* 10:305–308 (1992), demonstrate that the expression of a foreign ribosome-inactivating protein increases resistance to fungal disease in transgenic plants.

Thus, the present invention encompasses methods of protecting plants from fungal infections by transforming plants with vectors comprising the osmotin promoter and a foreign structural gene encoding chitinase, glucanase or ribosome inactivating protein. The present invention also contemplates the transformation of plants with a combination of such vectors to provide a synergistic effect.

In addition to methods of protecting plants from fungal infection, the present invention relates to methods for diminishing the impact of a fungal disease. Fungal endo α-1,4-D-polygalacturonases facilitate fungal colonization and plant nutrient release by solubilizing plant cell wall homo-α-1,4-D-galacturonase. Lamb et al., *Bio/Technology* 10, 1436–1445 (1992). Thus, vectors can be constructed comprising a foreign structural gene encoding an inhibitor of fungal endopolygalacturonase operably linked to an osmotin promoter. The cloning and characterization of a gene encoding a bean endopolygalacturonase-inhibiting protein is described by Toubart et al., *Plant J.* 2:367–373 (1992).

An osmotin promoter of the present invention can be used to control the expression of insecticidal toxin genes. Such insecticidal toxin genes include *Bacillus thuringiensis* δ-endotoxins. For example cryIA δ-endotoxins are highly toxic to lepidopteran insects, while cryIIIA δ-endotoxins are highly toxic to coleopteran insects. Geiser et al., *Gene* 48:109–118 (1986), disclose the cloning and nucleotide sequence of a cryIA(b) δ-endotoxin gene. The transformation of plants with vectors comprising a cryIA(b)δ-endotoxin gene has been described by Williams et al., *Bio/Technology* 10:540–543 (1992), Koziel et al., *Bio/Technology* 11:194–200 (1993), and Fujimoto et al., *Bio/Technology* 11:1151–1155 (1993). In addition, Lereclus et al., *Bio/Technology* 10:418–421 (1992), disclose the construction of a plasmid comprising structural genes encoding for cryIIIA and cryIAc. Thus, the present invention encompasses vectors comprising such δ-endotoxin genes under the control of the osmotin promoter.

The present invention also encompasses methods for protecting against nematode pathogens. Chitin is an integral part of the outer covering of nematodes, nematode eggs, and nematode cysts. Thus, the osmotin promoter/chitinase structural gene vectors, described above, are suitable for this purpose.

The present invention further comprises methods for protecting against viral infections. For example, the foreign structural gene can be a viral coat protein gene. The accumulation of viral coat proteins in transformed plant cells provides resistance to viral infection and/or disease development by the virus from which the coat protein gene was derived, as well as by related viruses. See Beachy et al., *Ann. Rev. Phytopathol.* 28:451–474 (1990). For example, coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

Alternatively, protection against viral disease can be achieved using a vector comprising mammalian 2'–5' oligoadenylate synthetase operably linked to an osmotin promoter. Truve et al., *Bio/Technology* 11:1048–1052 (1993), disclose the cloning and nucleotide sequence of a rat cDNA encoding 2'–5' oligoadenylate synthetase. Truve et al., also disclose that transgenic plants expressing 2'–5' oligoadenylate synthetase are protected against viral infection under field conditions.

In a third approach to providing protection against viral infection, an osmotin promoter of the present invention is used to direct the expression of antisense RNA. As discussed above, appropriate transcriptional and translational signals are required to express a foreign structural gene. According to the present invention, foreign structural gene sequences are operably linked to osmotin promoter sequences which control transcriptional expression in a transformed plant. Depending upon which strand of a double-stranded coding sequence is operably linked to the osmotin promoter, it is also possible to express antisense RNA. Since antisense RNA has a nucleotide sequence that is complementary to that of a specific mRNA, antisense RNA can hybridize with the corresponding mRNA and inhibit the mRNA translation. Therefore, the present invention encompasses the introduction of viral tolerance by transforming plants with a vector that expresses an antisense segment of a viral genome under the control of the osmotin promoter. For example, antisense RNA can be used to confer resistance to cucumber mosaic virus, as disclosed by Rezaian et al., *Plant Molec. Biol.* 11:463–471 (1988). Alternatively, antisense RNA can be used to resistance to tomato golden mosaic virus, as diclosed by Day et al., *Proc. Natl. Acad. Sci.* 88:6721–6725 (1991).

Also, purified osmotin is known to lyse sporangia and to inhibit growth of *Phytophthora infestans*. Accordingly, it could be possible to take advantage of the antifungal properties of a given osmotin protein by driving the osmotin gene with a mutant osmotin promoter which increases the expression of the protein at the site of fungal infection, increasing plant resistance.

Therefore, the present invention encompasses vectors comprising fragments of the osmotin promoter operably linked to the osmotin structural gene. Preferably, the osmotin promoter in such vectors contains nucleotides 5' of the osmotin gene extending at least to nucleotide −248. More preferably, the osmotin promoter in such vectors contains nucleotides 5' of the osmotin gene extending to nucleotide −1052. Such vectors can be constructed by replacing the GUS-encoding sequences of pBI101.1 or pBI201 derivatives, described below, with nucleotide sequences encoding the osmotin protein. These vectors are suitable for transformation of plants using Agrobacterium or a microprojectile delivery system, as shown herein. Osmotin-encoding nucleotide sequences can be obtained, for example, from pOC cDNA clones as described by N. K. Singh et al., *Plant Physiol.* 90:1096–1101 (1989).

The recombinant DNA molecule carrying the desired foreign structural gene under the control of the osmotin promoter sequence may be introduced into plant cell or tissue by any means known to the art. The technique used for a given plant species or specific type of plant tissue will depend on the known successful techniques. Means for introducing recombinant DNA into plant tissue include, but are not limited to transformation (J. Paszkowskie et al., (1984) EMBO J. 3:2717), electroporation (M. From et al., (1985) Proc. Natl. Acad. Sci. USA 82:5824), microinjection (A. Crossway et al., (1986) Mol. Ge. Genet. 202:179), or T-DNA mediated transfer from *Agrobacterium tumefaciens* to the plant tissue. There appears to be no fundamental limitation of T-DNA transformation to the natural plant host range of Agrobacterium. Successful T-DNA mediated transformation of monocots (G. M. S. Hooykaas-Van Slogtern et al., (1984) Nature 311:763–764), gymnosperms (A. M. Dandekar et al. (1987) Biotechnol. 5:5897–590) and algae (R. L. Ausich (1987) EPO Publication No. 108,580) has been reported. Representative T-DNA vector systems are generally described in the following references: An et al., (1986) EMBO J. 4:277; L. Herrera-Estrella et al., (1983) EMBO J. 2:987; L. Herrera-Estrella et al., (1985) in *Plant Genetic Engineering*, New York: Cambridge University Press, p. 63. Once introduced into the plant tissue, the expression of the structural gene may be assayed by any means known to the art, and expression may be measured at the transcriptional level or as protein synthesized. Techniques are known for the in vitro culture of plant tissue, and in a number of cases, for regeneration into whole plants. Procedures for transferring the introduced expression complex to commercially useful cultivars are known to those skilled in the art. Plant tissue transformed to contain the foreign genes of the present invention can be identified by the presence of the DNA fragments introduced, for example, using DNA hybridization assays. The presence of the introduced DNA fragments is an identifiable phenotype of the transformed tissue.

In order to promoter a further understanding and appreciation of the invention, the following Examples are provided. It will be understood that these Examples are illustrative and not limiting in nature.

EXAMPLES

The following Examples were carried out as described in Nelson et al., *Plant Mol. Biol.*, 19, 577–588 (1992); and Kononowicz et al., *Plant Cell*, 4, 513–524 (1992).

Cell Culture

Suspension cultures of tobacco (*Nicotiana tabacum* cv. Wisconsin 38) cells were maintained as described by Hasegawa et al., *L. Plant Cell Physiol*, 21, 1347–1355 (1980). Wild-type cells are designated as S-0 and cells adapted to 428 mM NaCl are designated as S-25. Filter-sterilized ABA was added to culture flasks 3 days after inoculation for treatment of suspension-cultured cells.

Preparation and Analysis of Nucleic Acids and Protein

RNA from cultured tobacco cells and plants was prepared by phenol/chloroform extraction and LiCl precipitation. DNA was prepared by phenol/chloroform extraction and CTAB precipitation. Nucleic acids were quantitated spectrophotometrically. Plant DNA was digested by various restriction endonucleases, separated on agarose gels, and transferred to reinforced nitrocellulose (Schleicher and Schuell). Hybridization conditions were as described by Singh et al., *Plant Physiol*, 90, 1096–1101 (1989). Filters were washed at room temperature in 1×, 0.2× and 0.1×SSPE sequentially with each wash containing 0.1% SDS. Osmotin protein was detected on western blots of proteins separated by SDS-PAGE reacted with anti-osmotin antibody isolated from chicken egg yolk.

Screening of Genomic Library

A Charon 4 *Nicotiana tabacum* leaf library (Eco RI as cloning enzyme) was screened by plaque hybridization utilizing $^{32}$p-labelled cDNA encoding osmotin (pOC 17) as probe and *Escherichia coli* NM519 as host. Three hundred thousand phage were screened and 2 clones that hybridized to pOC were isolated to plaque purity. By restriction endonuclease analysis, these clones were shown to be identical. Southern analysis of one of these clones, NT1, showed that Sac 1, Eco RI and Hind III released fragments of sizes 2.2 kb, 3.2 kb and 4.7 kb, respectively, that hybridized with osmotin cDNA. The coding region of osmotin lies near the center of the 4.7 kb Eco RI fragment. The 4.7 kb Eco RI fragment co-migrates with the Eco RI fragment from *Nicotiana sylvestris* which hybridizes with pOC but not with the Eco RI fragment from *Nicotiana tomentosiformis*, indicating that this gene is derived from the *N. sylvestris* parent of *N. tabacum*. The 4.7 kb Eco RI fragment which hybridized to pOC was subcloned into pTZ18 and designated as pOG.

Sequencing

A series of nested deletions in both directions of desired sequences was created by exonuclease III digestion (Erase-a-base, Promega). Sequencing was performed utilizing Sequenase 2.0 (USB). Approximately 3 kb of sequence between a Sal I site and a Hind III site was determined (Table 1, top) and a restriction map generated (Table 1, bottom). No introns were detected after comparison of the cDNA and genomic clones. The translation initiation begins 38 nucleotides from the transcription start site (Table 1, top). Putative CAAT and TATA boxes are underlined and transcription start sites are double underlined. The deduced amino acid sequence is indicated by single letter code. Putative polyadenylation sites are also underlined.

Primer extension

Two primer extension products differing in length by 4 nucleotides were detected in RNA from unadapted cells, unadapted cells treated with ABA and NaCl adapted cells (S-25). The length of the 5' untranslated region is approximately 40 bases. Either there are two start sites on each of the parental genes detected by hybridization to pOG (see, Singh et al., *Plant Physiol*, 90, 1096–1101 (1989)), or the start sites are slightly different for each of the two genes. In the osmotin gene, the distance between the transcription start site and translation start is identical to the distance between these two sites in the PR-S genes. See, Van Kan et al., *Plant Mol. Biol.*, 12, 153–155 (1989).

The primer used lies from nucleotide position 2078 to 2096 (Table 1) and corresponds to the 3' end of the sequence encoding the processed leader sequence of osmotin. $^{32}$P-end-labelled oligonucleotide was hybridized to 30 mg total RNA from S-0 cells, S-0 cells treated with 100 mM ABA for 24 hours and S-25 cells. The primer was extended utilizing reverse transcriptase and analyzed on a denaturing acrylamide gel.

S1 Nuclease Protection Assay

The upstream fragment (Cla II-Sal I) shown in Table 1 (bottom) was end-labelled at the Sal I site. End labelled fragments ($10^6$ cpm) were mixed with 20 mg of total RNA isolated from cell suspension cultures cells and dried under vacuum. The pellet was resuspended in 5 ml of 3M sodium trichloracetate, heated to 60° C. for 5 minutes and incubated at 42° C. overnight. S1 nuclease digestion was at 37° C. for 30 minutes in the presence of 100 ml S-1 mix (250 mM NaCl, 40 mM sodium acetate pH 5.5, 1 mM ZnSO$_4$, 20 mg/ml denatured salmon sperm DNA and 2000 U/ml S1 nuclease). The reaction was terminated by adding sodium dodecyl sulfate (SDS) and EDTA to a final concentration of 0.2% and 20 mM respectively, followed by phenol/chloroform extraction and precipitation with 0.3M ammonium acetate and 50% isopropanol. The precipitate was resuspended in 6 ml TE and 4 ml of stop buffer (95% formamide, 0.05% bromophenol blue, 0.05% xylene cyanol and 20 mM EDTA) and separated on a 6% polyacrylamide sequencing gel.

The levels of osmotin mRNA in each of the cells as determined by amounts of extension products agrees with earlier reported northern analysis data (see, Singh et al., *Plant Physiol*, 90, 1096–1101 (1989)) with much higher levels of mRNA accumulating in ABA treated unadapted cells and S-25 cells compared to unadapted cells. The S1 nuclease assay further confirmed the presence of two start sites and the distance to the translation initiation codon.

Nuclear Run-on Transcription Assay

Nuclei were isolated from suspension cultured cells according to the procedure of Lawton and Lamb, *Mol. Cell Biol.* 7, 335–341 (1987). Isolated nuclei were incubated in 0.1M ammonium sulfate, 4 mM $MgCl_2$, 0.3 mM phosphocreatine, 0.15 mg/ml creatine phosphokinase, 1 U/ml RNasin (Promega), 0.5 mL each ATP, CTP, GTP, and 2 mCi/ml $^{32}$P-UTP (3000 Ci/mmol). The standard reaction volume was 30 ml containing 15 ml nuclei. The reaction mixture was incubated 30 minutes at 30° C. Three units RQ1 DNAse (Promega) and 2 ml 20 mM $CaCl_2$ were added and the reaction mix incubated at 26° C. for 5 minutes. A mixture containing 1.5 ml proteinase K (2 mg/ml), 9 ml 10×SET (1×SET is 0.5% SDS, 5 mM EDTA, 10 mM Tris-HCl pH 7.4) and 50 mg yeast tRNA was added and the reaction was continued at 37° C. for 30 minutes. Labelled RNA was isolated by acid guanidinium/phenol/chloroform extraction. The assay consistently yielded $2-5\times10^6$ CPMs.

Plasmid DNAs were linearized with Eco RI, denatured and blotted onto supported nitrocellulose using a Schleicher and Schuell slot blot apparatus. Five mg were applied per slot. Labelled RNAs were hybridized to each set of plasmids in 0.3M NaCl, 10 mM piperazine-N,N'-bis[2-ethanesulfonic acid] (PIPES) pH 7, 10 mM EDTA, 0.4% SDS, 33% formamide and 0.2 mg/ml tRNA at 45° C. overnight with the probe concentration usually $4\times10^6$ CPMs per ml. Filters were washed three times, 30 minutes each wash, in 1×SSC, 0.1% SDS at 45° C. Filters were exposed to Kodak XAR5 film overnight-after which individual slots were cut out and counted by liquid scintillation counting.

Abscisic acid induces osmotin mRNA accumulation and transient translation of osmotin protein. See, Singh et al., *Proc. Natl. Acad. Sci. USA*, 84, 739–743 (1987) and Singh et al., *Plant Physiol*, 90, 1096–1101 (1989). These events are triggered by induction of transcription by ABA in suspension cultured cells. Treatment of 3-day-old S-0 suspension cultured cells with 100 mM ABA for 6 hours greatly enhances the rate of transcription. The level of transcription in control cells does not change significantly from the third to fourth day of culture. Except for 3-deoxy-D-arabino-heptulosonate-7-phosphate (DAHP) synthase, transcription of none of the control tobacco genes was induced by ABA treatment. Interestingly, DAHP synthase transcription was induced, indicating that the wound induced response of this gene (see, Dyer et al., *Proc. Natl. Acad. Sci USA*, 86, 7370–7373 (1989)) may be mediated through ABA, similar to the wound-inducible potato proteinase inhibitor II. See, Dyer et al., *Proc. Natl. Acad. Sci USA*, 86, 7370–7373 (1989). Northern analysis also indicated that DAHP synthase mRNA accumulates after 24 hour treatment with 100 mM ABA.

Construction and Testing of an Osmotin Promoter-GUS Fusion:

A 1.8 kb BqI II fragment (between position −1630 and +45 in Table 1) was inserted in the Bam HI site of pBI101.1. Jefferson et al., *EMBO J.*, 6, 3901–3907 (1987). The construct (features illustrated in FIG. 1) was introduced into *N. tabacum* L. cv. W38 by Agrobacterium-mediated tobacco leaf disk transformation. Plants were regenerated directly from leaf disks. Seed was obtained from three independent primary transformants (GUS1A, GUS1B, and GUS1C) and treatments were performed on segregating populations of at least 200 R1 seedlings. All of the experiments were repeated at least two times, by measuring GUS activity in two separate extracts for each experiment.

R1 seeds were germinated on two filter disks wet with 4 ml 0.1×MS salts in 9 cm Petri dishes under sterile conditions. For ABA and NaCl treatments, dishes were flooded with a solution containing the desired ABA or NaCl concentration, decanted, and 1 ml of fresh solution was added. Dishes for control and ethylene treatments received 1 ml water. For wounding experiments, leaf strips 1 cm wide were cut with a razor blade and floated on water. All treatments were kept in sealed PlasLab chambers with beakers containing 1M KOH as $CO_2$ traps. Norbornadiene (NBD) was added to 2000 mg/l and ethylene concentration determined on a Hewlett Packard 5730A Gas Chromatograph.

Seedlings and leaves were extracted with the buffer of Jefferson et al, *EMBO J.*, 6, 3901–3907 (1987). In experiments with NaCl treatments, samples were passed over Sephadex G-50 columns equilibrated with extraction buffer. Protein was determined with the Bio-Rad Bradford reagent assay. A volume of extract containing 100 mg protein was taken and brought to 100 ml volume with additional extraction buffer. The assay was initiated at 37° C. by adding 900 ml extraction buffer containing 1 mM 4-methylumbelliferyl glucuronide (MUG) and usually incubated one hour. The assay procedure gave activities that were linear with respect to time and amount of protein. Assays were stopped by adding 100 ml of the reaction to 900 ml 0.2M $Na_2CO_3$. The 4-methylumbelliferone (4-MU) fluorescense (365 nm excitation, 455 nm emission) was measured on a Perkin Elmer LS-5 Fluorescense Spectrophotometer standardized to 1 mM 4-MU.

Three independent transformants (GUS1A, B and C) containing the osmotin promoter-GUS fusion were studied. These three contained varying numbers of introduced genes as determined by Southern analysis utilizing the GUS-coding region as probe. Digestion of DNA with Eco RI results in the observation of two copies in GUS1A, at least three copies in GUS1B, and one copy in GUS1C. Double digestion with Eco RI and Sal I gave single bands which comigrated with an Eco RI and Sal I fragment cut from the pBI121.1-derived vector used in transformation. The single intensity of these bands correlated with the number of copies observed in the digests with Eco RI alone. GUS1C contains one copy, GUS1A two copies and GUS1B contains at least three copies. A fourth band of significantly weaker intensity than the rest was reproducibly observed in GUS1B.

Figure 2:
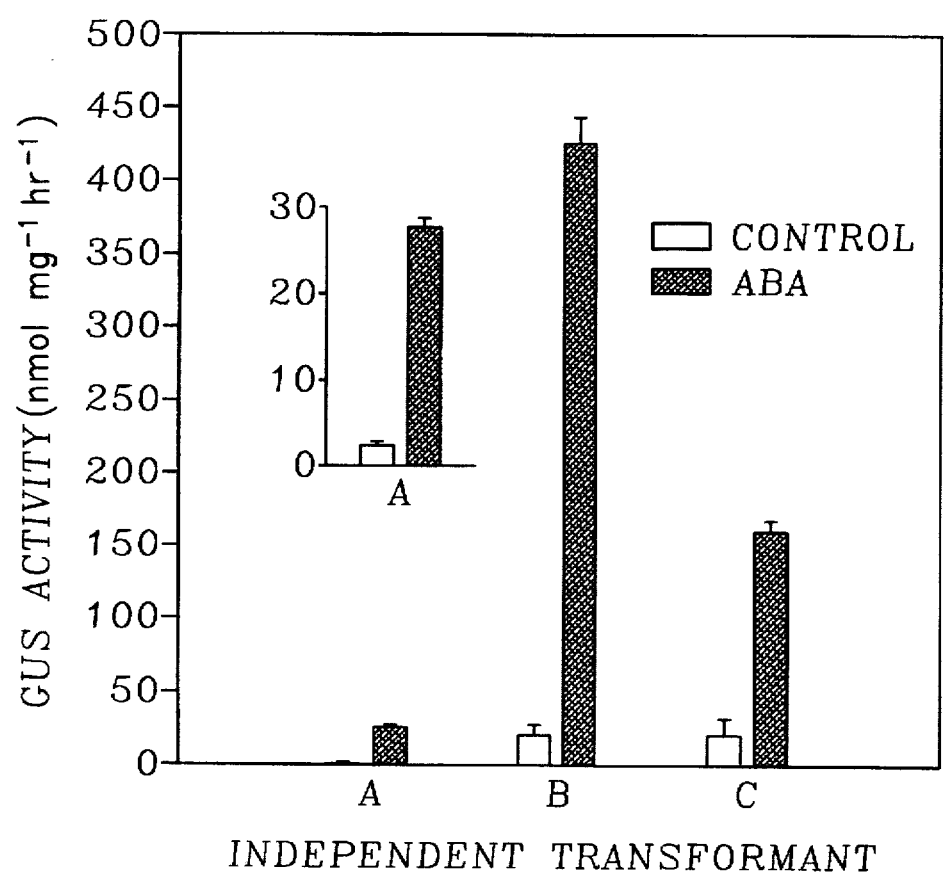
FIG. 2 shows GUS activity of transformants of the
invention under control conditions and as induced by ABA.

Characterization of ABA effect on GUS activity:

In all three independent transformants, GUS activity was highly inducible in four-day-old R1 seedlings by treatment with 100 mM ABA for 24 hours (FIG. 2). GUS activity increased 11, 18 and 7-fold in GUS1A, B and C seedlings, respectively. GUS activity levels were highest in GUS1B seedlings and lowest in GUS1A seedlings. Steady state specific GUS activities varied in the three transformants most likely because of integration position effect. The level of GUS activity was similar after ABA treatment of levels observed in expression assays of the rab-16a and Em genes. See, Marcotte et al., *Nature.* 335, 454–457 (1988) and Yamaguchi-Shinozaki et al., *Plant Mol. Biol.* 15, 905–912 (1990). GUS1B seedlings were utilized in more detailed studies on the effect of ABA on the osmotin promoter as reported below.

Figure 3:
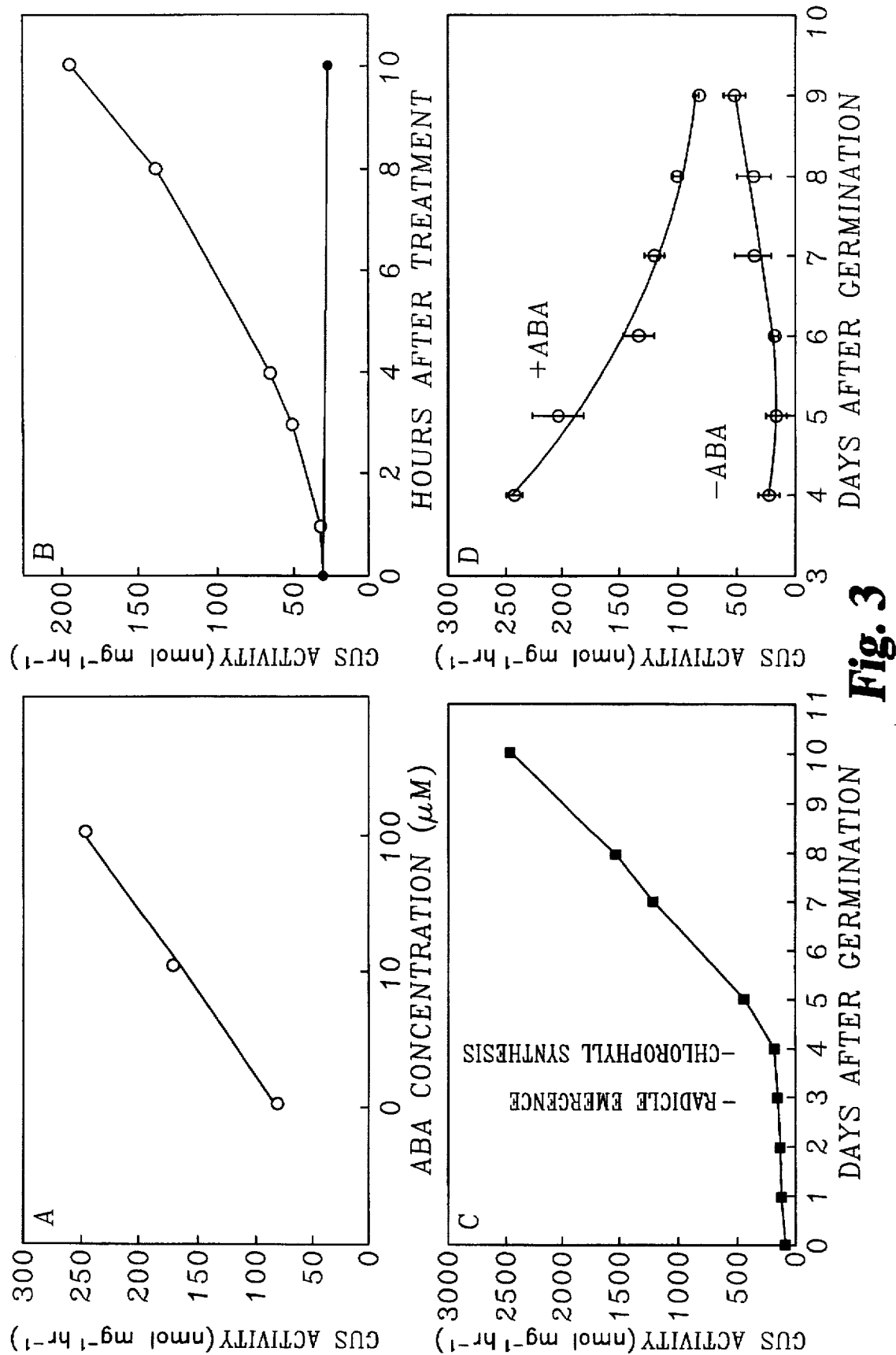
FIG. 3 shows GUS activity assays of ABA treated trans-
formed seedlings of the invention illustrating dose response (A), kinetic induction (B) and growth stage dependence (C and D). Open circles are for ABA treatments and closed circles are for controls.

Dose Response and Kinetics of Induction:

The osmotin promoter activity shows a linear response to ABA when compared to the log of hormone concentration (FIG. 3A). For FIG. 3A, four-day-old GUS1B R1 seedlings were treated for 24 hours with the indicated concentrations of ABA. With regard to kinetics of induction, following treatment of four-day-old GUS1B R1 seedlings with 100 mM ABA, GUS activity begins to increase within one hour and increases continuously for 24 hours (FIG. 3B; data shown for up to 10 hours).

Developmental Control Over ABA Response:

FIG. 3C shows a growth curve based on fresh weight for GUS1B seedlings (average weight of at least 30 pooled seedlings weighed on a Mettler-balance). Three days following imbibition, radicals emerge and one day later, chlorophyll synthesis is evident. Once photosynthesis begins, seedlings rapidly develop. However, the sensitivity of seedlings to ABA decreases and by day 9 is only slightly higher than the controls (FIG. 3D). For FIG. 3D, GUS1B R1 seedlings were treated on the indicated days after germination with 100 mM ABA and assayed 24 hours later. Treatments were replicated on seedlings germinated in separate petri dishes and assayed separately.

Both root and leaf tissues lost sensitivity to ABA as the seedlings developed (See Table 2B below). This decrease in ABA responsiveness is not due to limitation of growth since fresh weight gain remained rapid and linear over the time period studied.

TABLE 2

Relative activity of β-glucuronidase in shoots and roots of GUS1B. Specific activity was measured as nmol mg$^{-1}$h$^{-1}$.
A. For each experiment, roots and shoots from 20 seedlings (5 days old) together in one Petri dish were dissected from each other at the transition zone, extracted and assayed separately. Four separate experiments were performed. The data are presented relative to the observed specific activity in the shoots of each experiment.
B. On the days indicated, seedlings were treated with 100 mM ABA for 24 hours. Seedlings were dissected and assayed as described above. The data are presented as fold higher activity in ABA-treated tissue as compared to untreated tissue.

| A. Experiment | 1 | 2 | 3 | 4 |
|---|---|---|---|---|
| Root | 12.8 | 16.5 | 20.3 | 13.8 |
| Shoot | 1.0 | 1.0 | 1.0 | 1.0 |

| B. | Day 6 | Day 7 |
|---|---|---|
| Root | 15.1 | 7.0 |
| Shoot | 3.8 | 1.8 |
| Whole Seedling | 7.1 | 3.3 |

Other Transcriptional Activators:

Ethylene at 20 mg/l induces osmotin mRNA accumulation in plants at all stages of development, unlike the response to ABA discussed above. GUS enzyme activity was measured following 24 hour treatments of GUS1B R1 seedlings with 5 mg/l ethylene on days 4, 5, and 6 after germination of GUS1B seedlings (FIG. 4A). In FIG. 4, each bar is the average of data from 6 experiments (2 each from days 4, 5 and 6 after germination). The error bars indicate the standard deviation. As can be seen, the ethylene increased promoter activity 2.5 fold.

It was observed that wounding GUS1B R1 seedlings induced GUS enzyme activities 2- to 10-fold, but there was considerable variation in this response, most likely due to variations in degree of wounding. 2,5-norbornadiene (NBD), the ethylene action inhibitor, reverted the induction by wounding suggesting that the wound response of the osmotin promoter is likely an ethylene mediated wound response.

NaCl treatments (200 mM) induce GUS enzyme activity over a 24 hour period by 3.2 fold (FIG. 4B). For FIG. 4B, GUS activities of GUS1B R1 seedlings were measured for response to 24 hour treatments with the indicated concentrations of NaCl. Each treatment was replicated twice on four-day-old seedlings. The response of young seedlings to NaCl is possibly mediated through ABA rather than ethylene, since NBD did not reverse the increase in enzyme activity.

Additional evidence for a difference in response of the osmotin promoter to ethylene and ABA is the change in sensitivity with respect to age of treated seedlings (FIG. 5). The data in FIG. 5 were obtained by measuring for response to 24 hour treatments with 100 mM ABA and 5 ng/l ethylene on the indicated days after germination. The data are expressed as fold increases over the controls for each treatment for each day. Each data point is the average of two replicated treatments. While sensitivity to ABA decreased with age, sensitivity to ethylene remained more constant. This result is confirmed by northern analysis of leaf tissues which accumulate osmotin mRNA in response to ethylene treatment at any age while only young leaves, not older leaves, accumulate osmotin mRNA in response to ABA treatment.

TISSUE SPECIFICITY OF OSMOTIN PROMOTER (OSM) ACTIVITY:

The above-described studies demonstrated that the activity of the osmotin promoter is approximately 16-fold higher in roots than in shoots per mg protein (Table 2A). This result is in agreement with results from Western analysis of osmotin and the basic PR proteins which indicate that the tissue with the highest levels of protein accumulation is the root, at least when analyzed relative to total protein. The sensitivity to ABA of the osmotin promoter in both root and shoot tissues decreases with age (Table 2) similar to the decrease seen for intact seedlings (FIG. 3D).

In additional studies, the following tissue-specific expression patterns were discovered by study of GUS1B plant transformants. For these additional experiments, vegetatively propagated transgenic tobacco plants carrying the OSM::GUS chimeric gene or the GUS gene without the OSM promoter were grown hydroponically in quarter-strength MS salts (Murashige et al., *Physiol. Plant,* 15, 473–497 (1962)) and adapted stepwise to a concentration of 170 mM NaCl by increasing the NaCl concentration by 42.5 mM every 3 days. Plants were grown in the presence of 170 mM NaCl for 4, 8, and 12 weeks before tissue samples were taken for GUS analyses. Hydroponically cultured plants of the same age grown without NaCl were used as unadapted controls.

The GUS enzyme assay was used to measure the relative activity of the OSM promoter in OSM::GUS gene fusion transformants. Histochemical staining for GUS activity was performed according to the procedure of Jefferson et al., *EMBO J.*, 6, 3901–3907 (1987), with the modifications proposed by Koltunow et al., *Plant Cell*, 2, 1201–1224 (1990). Samples of plant tissues and organs were fixed for 15 minutes under vacuum in 0.1M sodium phosphate buffer, pH 7.0, containing 0.1% formaldehyde, 0.1% Triton X-100, and 0.1% β-mercaptoethanol. Samples were then rinsed several times with 0.1M phosphate buffer containing 0.1% β-mercaptoethanol, followed by a rinse with 0.05M phosphate buffer, pH 7.0. For the GUS reaction assay, a buffered solution (0.05M sodium phosphate buffer, pH 7.0) of 1 mM 5-bromo-4-chloro-3-indoyl-β-D-glucuronic acid cyclohexylammonium salt (Biosynth AG, Staat, Switzerland) containing 0.1% β-mercaptoethanol and 0.1% Triton X-100 was used. After the GUS reaction, organ or tissues samples were fixed for 4 hours in a 2% glutaraldehyde solution in 0.05M phosphate buffer, pH 7.2, or 10% formaldehyde, 20% ethanol, 5% acetic acid. Chlorophyll was extracted from tissues during dehydration in an ethanol series prior to embedding in Tissue Prep 2 embedding wax (Fisher Scientific, Fair Law, N.J.). Paraffin sections (10- to 50-mm-thick) were cut and deparaffinized. Slides were viewed and photographed using a microscope (Optiphot model; Nikon, Tokyo) set for bright-field illumination or Nomarski differential interference contrast.

For pollen grains, along with the procedure described above, the GUS assay proposed by Kosugi et al., *Plant Sci.*, 70, 133–140 (1990) was used to eliminate intrinsic GUS activity by the addition of methanol at 20% volume to the GUS assay mixture.

The following results were obtained:

A. Patterns of Expression of OSM::GUS Gene Fusion in Vegatative Organs of Unadapted Plants:

GUS activity was analyzed in the longitudinal and transverse paraffin sections of roots, in stem internode segments (basal, middle, and apical segments), and in leaves at different stages of development. Low GUS activity was detected in tissues of roots, stems, leaves and reproductive organs of transformed unadapted plants. Although osmotin and other basic PR proteins are considered to accumulate in healthy roots, we found that the expression of the OSM-::GUS gene was quite low in unstressed hydroponically grown roots. However, high GUS activity was detected in roots of these plants when grown in either soil or vermiculite. A higher level of the GUS activity was observed in the epidermis of both roots (in the elongation zone) and trichomes and epidermis of basal leaves and stems. No GUS activity was detected in either vascular or parenchymatous tissues of any vegetative plant organs. Some minor variation in GUS activity (i.e., differences in color intensity but not localization) was observed between analyzed organ samples.

B. High GUS Activity in Mature Pollen Grains After Anther Dehiscence:

GUS activity was analyzed in tissues of different parts of flowers at several developmental stages. Only mature pollen grains and epidermis of petals showed GUS activity. No GUS activity was observed in any other floral tissue by histochemical GUS assays.

C. Expression of the OSM::GUS gene in pollen grains occurred after anther dehiscence:

Approximately 57% of the pollen grains expressed moderate or high levels of GUS activity. Another 30% showed low GUS activity. This variability in degree of expression could be the result of segregation of the four OSM::GUS genes carried by GUS1B plants. GUS activity decreased rapidly after the initiation of pollen germination in vitro.

After 24 hours of culture on pollen germination medium, almost all (93%) of the pollen grains showed no GUS activity. At no stage of development or germination was moderate or high GUS activity found in pollen grains from nontransformed tobacco plants or plants transformed with a construct consisting of the GUS coding sequence without the OSM promoter. Only occasionally were pale blue-stained pollen grains observed in these plants.

When mature pollen grains from transformed OSM::GUS plants were incubated in a GUS assay mixture with 20% methanol, a treatment that according to Kosugi et al., *Plant Sci.*, 70, 133–140 (1990) eliminates the intrinsic GUS activity in tobacco plants, color intensity was slightly reduced, but the percentage of GUS-positive grains did not change (approx 90%). GUS activity was not detected in pollen grains from nontransformed plants and plants transformed with GUS coding sequence alone (without promoter) when GUS assay was conducted in the presence of 20% methanol.

D. Induction of the OSM Promoter During Fruit Development:

Before fertilization and fruit formation, the only tissue of the ovary that expressed GUS activity was the vascular tissue in the basal portion of this floral organ. In the ovary of both NaCl-adapted and NaCl-unadapted OSM::GUS-transformed tobacco plants, induction of GUS activity and a gradual increase in GUS intensity were observed at the final stages of fruit development as desiccation of the fruit began. Interestingly, a GUS-positive reaction was found only in the maternal tissues of developing fruit (pericarp and placenta) during desiccation, but not in seeds at any stage of development, including mature, desiccated seeds.

E. Adaption to NaCl Induces and/or Stimulates Activity of the OSM Promoter:

Long-term adaptation of OSM::GUS transgenic plants to moderate concentrations of NaCl (171 mM) modulated the activity of the OSM promoter in temporal and spatial contexts. Paraffin sections were made of roots, stems, and leaves at different stages of the development from both types of transgenic plants as well as nontransformed tobacco plants that were adapted for 30, 60 and 90 days to NaCl and used to localize GUS activity. Histochemical analysis of GUS activity was also performed at different stages of flower development, before and after pollination (stages 1, 3, 5, 7, 8, 9, 11, and 12 according to the designation proposed by Koltunow et al., *Plant Cell*, 2, 1201–1224 (1990)), and at different stages of fruit formation. GUS activity was carefully monitored in pollen grains during their development and in vitro germination.

F. Adaption to NaCl in Roots:

OSM::GUS transgenic plants adapted to grow in NaCl for 30 days showed increased GUS activity in root elongation zones (epidermis and root cortex parenchyma) but not in root apical meristems. After prolonged (60 days) adaption of plants to NaCl, GUS activity was also observed in the endodermis, cortex, and tissues of the vascular cylinder within the root elongation zone. A GUS-positive reaction was never found either in root meristems or in any tissue of the differentiated (basal) zone of the root.

G. Stem Adaption to NaCl:

Adaption to NaCl also increased OSM promoter activity in stem internodes at all stages of plant development. The GUS-positive reaction was restricted to the epidermis and the xylem parenchyma of the stem, but was also occasionally observed in the cortex parenchyma. The pattern of expression or GUS level in these tissues did not change significantly after the initial induction by NaCl.

H. Leaf Adaptation to NaCl:

Although increased activity of the OSM promoter was found in the trichomes, epidermis, mesophyll, and xylem parenchyma of fully developed (expanded) leaves after adaptation to NaCl, the strongest GUS-positive reaction was found in leaf tips. In young leaves, lower GUS activity was observed in the trichomes. No GUS activity was observed in either shoot apical meristems or leaf primordia. There was a consistent gradient of low to high OSM promoter expression in the youngest to the oldest leaves, and this was confirmed with GUS fluorometric assays using 4-methylumbelliferyl β-D-glucuronide substrate.

I. Adaption to NaCl in Reproductive Structures:

Adaptation of transgenic OSM::GUS plants to NaCl significantly affects OSM promoter activity in flowers. Moderate GUS activity after salt adaptation was found in vascular bundles of the basal part of the ovary, the epidermal layers and the mesophyll of the top (limb) region of petals, and in the epidermis and mesophyll of the sepal tips.

A high level of OSM::GUS gene expression was found in mature pollen grains of adapted and unadapted plants at anther dehiscence. The GUS-positive reaction, however, was visible only in mature, "dry" pollen grains and decreased dramatically during the early usages of in vitro germination.

FURTHER CHARACTERIZATION OF OSMOTIN PROMOTER

A. Developmental Control of the Osmotin Promoter

Transcriptional activation of the tobacco OSM promoter by different inducers was further analyzed in the R1 progeny of transgenic tobacco carrying copies of the OSM promoter (−1630 to +45) (Table 1) fused to the GUS reporter gene. Evaluations of OSM:GUS fusions indicated that the cis regulatory elements for transcriptional activation by ABA, ethylene and NaCl are contained in this promoter fragment. However, patterns of chimeric gene expression in transgenic seedlings clearly indicated differential regulation of the OSM promoter by these inducers. Exogenous ethylene and NaCl-stress induce OSM promoter activity in 4-day-old seedlings to a much lesser degree than ABA (2.5-fold, 3.2-fold and up to 18-fold, respectively). Further, whereas sensitivity of OSM promoter to ethylene remains relatively constant with age of seedlings, sensitivity to ABA, in both roots and shoots, reaches its maximum in 4-day-old seedlings and then rapidly decreases. These results indicate developmental control over sensitivity of the OSM promoter to ABA.

B. Analysis of Osmotin Promoter Cis-and Trans-Acting Factors

1. Methods

Plant Material

Tobacco (Nicotiana tabacum var. W-38) shoots were maintained in cultures on modified MS media containing 0.1 mg/L BA (MS salts, 30 g of sucrose, 100 mg myo-inositol, 400 mg thiamine.HCl, made up to one liter; pH 5.7). Young leaves harvested from shoot cultures 15 days after transfer were used in transient expression studies. Tobacco plants grown under controlled environmental chambers were used for other experiments. Tobacco cell cultures adapted to grow in the absence of salt (S-0) and in the presence of 428 mM NaCl (S-25) were maintained as described above. Filter-sterilized ABA was added to control cell cultures to a final concentration of 100 μM and cell cultures were allowed to grow for 24 h before harvesting for isolation of nuclei. Tobacco plants with six fully developed leaves were also exposed to 5 ppm ethylene for 24 h, and harvested for isolating nuclear proteins.

Vector construction

An osmotin promoter, 2 kb in size (SalI-SalI fragment), was cloned into pGEM3 (Promega, USA). Different 5' deletion fragments were generated by Exo III using an Erase-a-Base kit from Promega. The extent of deletion was confirmed by sequencing the 5' end of deleted clones. The HindIII-BglII restriction enzyme fragments obtained from the above plasmids were further subcloned into a HindIII-BamHI digested plasmid (pBI201; Jefferson et al., *EMBO J.*, 6:3901–3907 (1987)), containing a promoter-less GUS reporter gene. These plasmids along with a plasmid (pDO221; provided by Dr. David W. Ow, Plant Gene Expression Center, USDA, Albany, Calif.) containing luciferase gene as control were used for studying transient expression of the reporter gene.

Preparation of microprojectiles

Tungsten and gold particles were prepared according to the instructions provided by the manufacturer (Du-Pont Biolistic). Tungsten particles (1.1 μm) were used to deliver DNA using PDS-1000 particle delivery system, whereas, gold particles (1.5 to 3.0 μm diameter) were used for DNA delivery by Biolistic PDS-1000 He system. The DNA delivery was optimized for particle size, distance between the tissue and particle discharge barrel, bombardment pressure (He gun).

Inducer treatment

After DNA delivery, leaves were placed on wet filter paper. The treatments were initiated by placing the tissue for 24 h on wet filter papers soaked with NaCl (171 mM), ABA (100 μM) or water (control). Tissues were also exposed to ethylene (5 ppm) or wounded by cutting into small strips. Some of the wounded tissue was exposed to the ethylene action inhibitor norbornadiene (NBD, 2000 ppm). All the experiments were repeated at least three times with three replicates each.

Enzyme assays

Twenty four hours after inducer treatments, the leaves were homogenized with the luciferase-GUS extraction buffer (50 mM $K_2HPO_4$; pH 7.8, 1 mM EDTA, 10 mM DTT and 5% glycerol) using a polytron homogenizer. The homogenate was spun at 12,000 g for 2 min in a microcentrifuge and the supernatant was collected. The supernatant was used for protein determination by Bradford reagent assay and for measuring luciferase (LUX) and glucuronidase (GUS) enzyme activity.

In general, bombardment of the tissue resulted in random distribution of particles. In order to overcome this inherent variability another reporter gene, luciferase, driven by the cauliflower mosaic virus 35S promoter (CaMV35S) was used as a control. Fifty microliters of extract were mixed with 100 μl of luciferase buffer (50 mM HEPES: pH 8.0, 20 mM $MgCl_2$, 10 mM ATP and 50 mg/ml BSA) in a glass cuvett (Kimble culture tubes) and placed in a Chem-Glow photometer (Aminco, USA). The luciferase reaction was initiated by injecting 50 μl of 1 mM luciferin. The light produced by chemi-luminescence was measured. For GUS measurements, leaf extracts containing 100 μg of protein were made up to 200 μl with extraction buffer. The GUS assay was started by adding 800 μl of extraction buffer containing 1 mM 4-methyl umbelliferyl glucuronide (MUG) and incubated at 37° C. The assay was terminated by adding 200 μl of reaction mix to 800 μl of 0.2M $Na_2CO_3$. The end product of the reaction, 4-methylumbelliferon (4-MU) was measured in a Perkin Elmer LS-5 fluorescence spectrophotometer (365 nm excitation and 455 nm emission) standardized to 1 µM 4-MU.

Isolation of nuclear proteins and gel retardation assay

Nuclei were isolated from cell cultures and leaves as described by Lawton et al., *Plant Physiol.* 93, 1370–1375 (1990). The nuclear protein extracts were prepared by the protocol described by Miskimins et al., *Proc. Natl. Acad. Sci.* 82, 6741–6744 (1985). Different osmotin promoter fragments shown in FIG. 2, were end labeled with γ-($^{32}$p) ATP. The binding reactions were carried-out in 15 µl solution containing 0.5 ng of labeled DNA, 2 µg of nuclear extract, 2 µg of poly dI-dC, 10 mM Tris-HCl (pH 7.5), 50 mM DTT, 1 mM EDTA and 10% glycerol at 30° C. for 30 min. The amount of poly dI-dC added to the assay mix was determined by a titration experiment. This concentration (2 µg) was sufficient to overcome non-specific binding of proteins to DNA. The reaction products were separated on 4% polyacrylamide gels as described by Singh et al., *Nature* 319, 154–158 (1986). The dried gels were exposed to X-ray films with intensifying screens for 12 to 24 h.

DNaseI foot printing assay

DNase I foot printing assay was performed according to the procedure described by Andrisani et al., *Mol. Cell. Biol.* 8, 1947–1956 (1988). A ClaI-ClaI fragment (nucleotide −762 to −642) showing specific binding with nuclear extracts was used for the DNaseI foot printing assay. The ClaI-ClaI fragment was end labeled by filling the 5'ClaI site with γ-($^{32}$p) dCTP, and was isolated by polyacrylamide gel electrophoresis. The end labeled fragment (20,000 cpm) was incubated with 20 µg of nuclear protein isolated from salt adapted cells in a typical DNA binding assay described above at 30° C. for 30 min. The reaction mixture was subjected to DNaseI treatment for 2 min. The reaction was terminated by the addition of 100 µl of 30 mM EDTA, 1% SDS, 300 mM NaCl and 250 µg of tRNA per ml. Samples were extracted with phenol-chloroform, followed by ethanol precipitation and loaded onto a denaturing polyacrylamide sequencing gel. A known sequencing ladder was used to determine the size of the protected region.

2. Comparative Analysis of the Osmotin Gene Promoter Sequence

Comparison of the osmotin promoter with other ABA induced genes revealed the presence of regions of similarity with the ABRE (ABA responsive element, FIG. 6). The ABRE is known to contain a core sequence "CACGTG" (G-Box), which is present in several genes regulated by ABA. However the sequence present in the non-coding strand of osmotin promoter (nucleotides −241 to −235) is slightly different from that of others, in that it contains an extra nucleotide T(5'-GTGTCAC-3') in the middle of 5'-CACGTG-3'sequence. Furthermore two other sequences, CAAGTG and CACGTT, showing high degree of identity with G-Boxes are also found overlapping this G-Box core element. The conserved motif I (ACGTGGC) of the ABA responsive gene, rab 18, is also present in the non-coding strand upstream of nucleotide −248 (nucleotides −508 to −502) Several regions having high degree of identity with the activation sequence-1 (as-1) of the CaMV35S promoter (TGACG) are also present in the osmotin promoter (FIG. 6). The osmotin promoter also contains a sequence, in the non-coding strand (nucleotides −994 to −982), having 75% identity with a promoter element of the E-8 gene, that has been shown to be associated with tomato fruit ripening. Cordes et al., *Plant Cell* 1, 1025–1034 (1989). Osmotin gene expression also increased during late fruit development in tobacco. Kononowicz et al., *Plant Cell* 4, 513–524 (1992).

The upstream region of the osmotin promoter (nucleotides −1545 and −1634) contains a nucleotide sequence which is similar to the cis element H-Box. Loake et al., *Proc. Natl. Acad. Sci.* 89, 9230–9234 (1992). Several other direct and indirect repeats are also indicated by the underlined promoter sequence (FIG. 6). One of the interesting features of this promoter is the presence of an 82 bp inverted repeat with 93% identity at the 5' end.

3. Deletion Analysis of the 5'-Flanking Region of the Osmotin Promoter

In order to further understand the regulation of the osmotin promoter by different inducers and to define the specific regions of the promoter that are involved in osmotin gene activation, the pattern of expression of the GUS reporter gene (in pBI201), cloned to a series of 5' deletions of the osmotin promoter was examined in transient expression assays. As a control, plasmids containing the luciferase gene driven by the CaMV35S promoter were introduced simultaneously with osmotin-GUS constructs.

Figure 7:
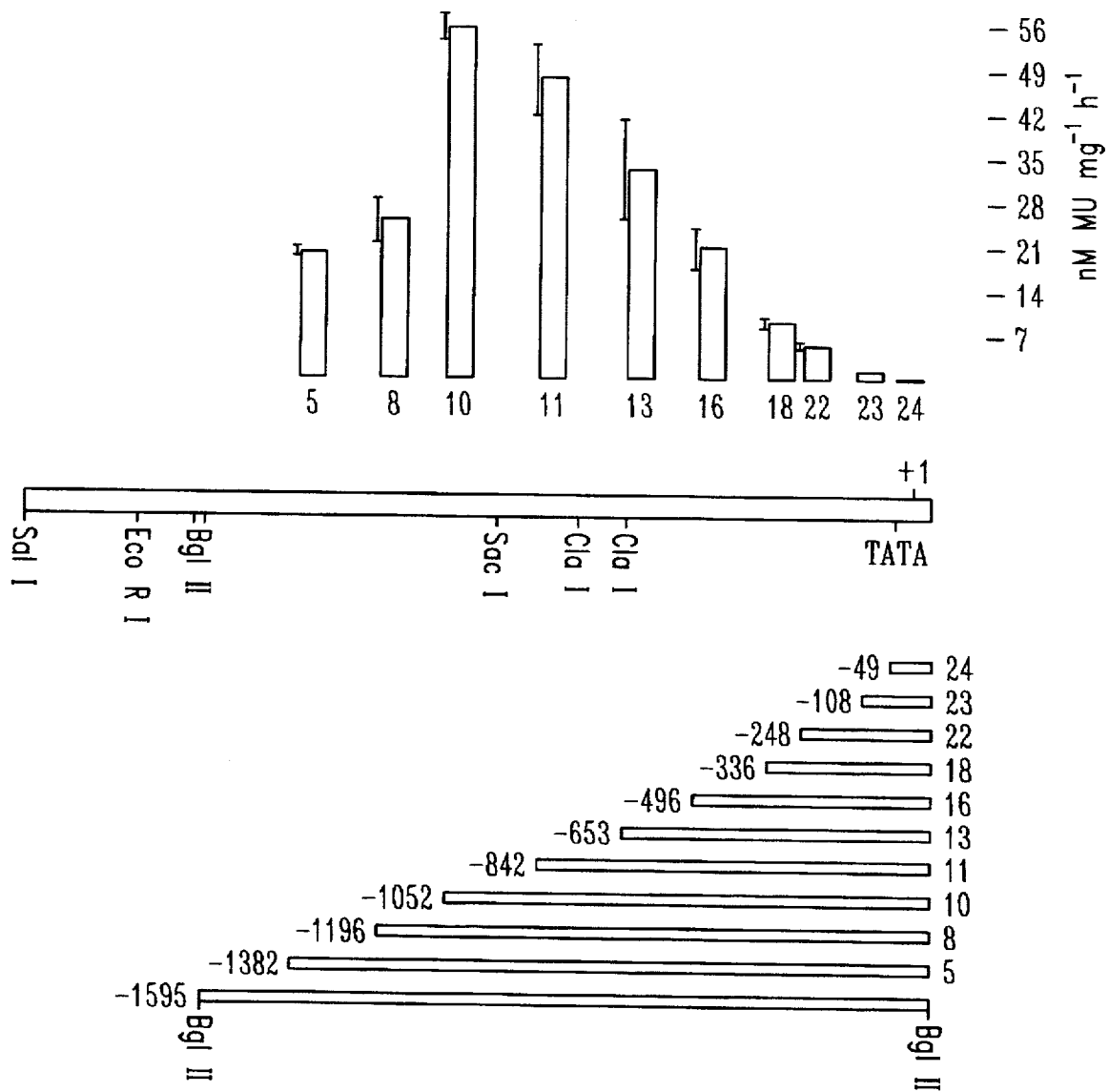
FIG. 7 shows transient expression of reporter gene GUS fused to different lengths of the osmotin promoter. Levels of GUS expression (nmol MU/mg protein/h) corresponding to increasing lengths of the osmotin promoter are shown in the histogram along with the restriction enzyme map. The vertical bars represent standard errors.
Figure 8:
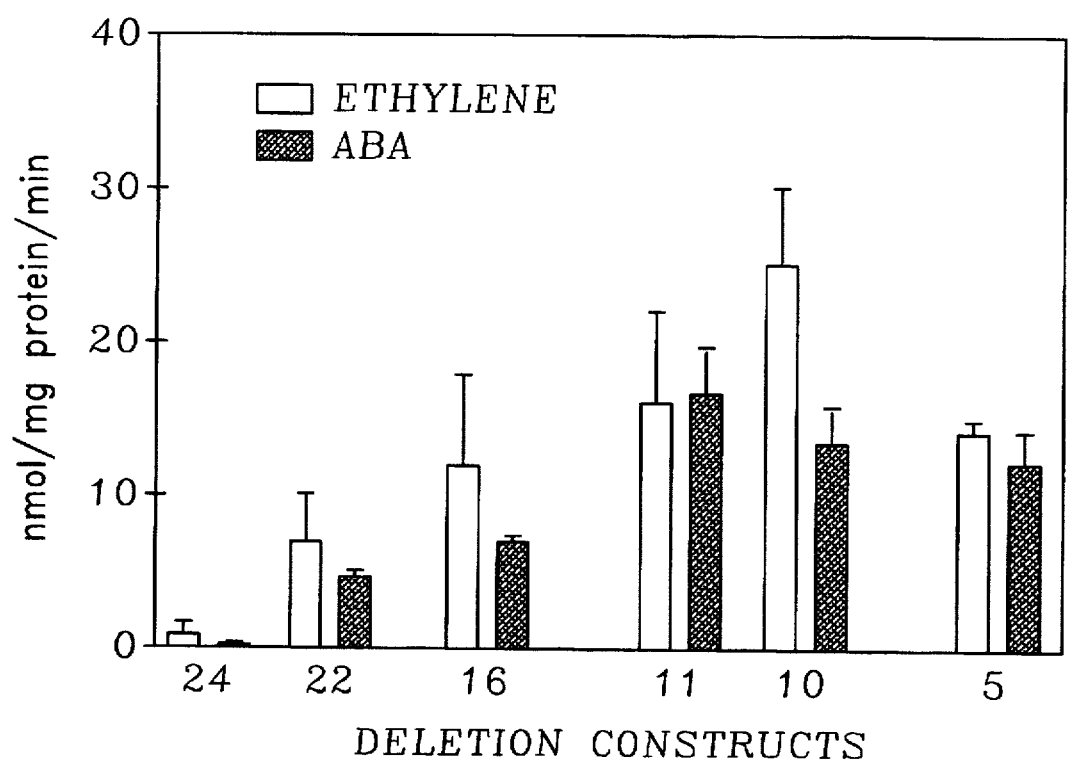
FIG. 8 shows the effect of ethylene and ABA on transient expression of the GUS reporter gene. Plasmids carrying different lengths of the osmotin promoter and CaMV35S-luciferase gene were coated onto gold particles and used for bombarding tobacco leaves via a Biolistic-1000 Helium gun. Following bombardment, the leaves were treated for 24 h in the presence of 100 µM ABA or 5 ppm ethylene. The leaves without any treatment represents control. GUS activity in the absence of treatment was subtracted from GUS activity in the presence of either ABA or ethylene. The net increase in GUS activity in response to ethylene and ABA treatment is presented in the histograms. The vertical bars represent standard errors. Deletion constructs were numbered as indicated in FIG. 7.

Studies demonstrated that bombarding the leaves with particles carrying the reporter gene and different lengths of the osmotin promoter, resulted in different levels of GUS expression even in the absence of any added inducer (FIG. 7). A DNA fragment representing nucleotides −248 to +45 provided a promoter suitable to actively transcribe the GUS reporter gene. Additional studies have demonstrated that a DNA fragment representing nuclotides −108 to −248 also provides for the active transcription of the GUS reporter gene. Fragments up to nucleotide −108 or nucleotide −49 containing the TATA and TATA+CAAT boxes respectively, were not sufficient to induce GUS. High level GUS expression was achieved with a DNA fragment extending from nucleotide +45 to nucleotide −1052, while any further increase in the promoter size decreased the GUS activity. The pattern of GUS expression in the presence of ABA and ethylene (FIG. 8) was similar. However, these inducers clearly caused enhanced expression of the reporter gene after delivery by particle bombardment. The GUS activity of NBD-treated tissue was lower than that of untreated tissue (Table 3), suggesting that wound-induced ethylene is at least in part responsible for the reporter gene expression. This result is not very surprising, since shooting the leaves with tungsten particles causes severe disruption (wounding) of tissue at the site of impact, and thus likely leads to the production of ethylene.

TABLE 3

Effect of wounding and ethylene action inhibitor NBD on transient expression of reporter gene (GUS). Plasmids containing the osmotin promoter (a DNA fragment containing nucleotides −248 to +45) and GUS reporter gene, and CaMV35S-luciferase gene were delivered to tobacco leaves by particle bombardment. The leaves were wounded after DNA delivery by cutting into strips. Some of the wounded leaves were exposed to the ethylene action inhibitor norbornadiene (2000 ppm) for 24 h. The luciferase activity was used to normalize the GUS activity.

| Treatment | GUS activity (nmol/mg protein/h) |
| --- | --- |
| Control | 35 + 1.5 |
| Wounding | 52 + 2.5 |
| Wounding to NBD | 20 + 0.5 |

Further characterization of the OSM promoter was performed on transgenic tobacco plants carrying a GUS coding sequence driven by different 5' deletion fragments of the promoter. Chimeric gene expression was analyzed in 5-dayold seedlings that were subjected to various treatments including: 100 mM ABA, 5 ppm ethylene, and 171 mM NaCl. The pattern of OSM::GUS gene expression in transgenic seedlings was similar to that obtained in transient experiments performed on tobacco leaves. High level expression of GUS activity was found with a −1052 to +45 promoter fragment, whereas a −248 to +45 promoter fragment also gave basal expression. No measurable GUS expression was detected with the −106 to +45 promoter fragment. ABA and NaCl were shown to be strong inducers of OSM promoter fragments both in transgenic seedlings and in leaf tissues examined by transient expression assays; ethylene induced the reporter gene to a much lesser extent in these tissues. No differences were found in the cis-element patterns of promoter induction by salt and hormone treatments.

4. Nuclear Protein Interactions with the 5' Region of the Osmotin Gene

To ascertain the presence of specific DNA sequences in the OSM promoter that interact with various trans factors, gel shift assays were conducted. Two DNA fragments, one close to the TATA box (nucleotides −108 to +45) and another upstream from the TATA box (ClaI-ClaI fragment; nucleotides −762 to −642), specifically interacted with nuclear factors as indicated by retardation of their mobility in a 4% polyacrylamide gel. This DNA binding activity was present both in control and treated cells and tobacco leaves. However, the abundance of binding factors significantly increased following the treatment with ABA, ethylene and in NaCl-adapted cells.

The ClaI-ClaI DNA fragment, designated EN-1, was chosen for further analysis because the DNA fragment is characterized by enhancer-like activity and strong DNA binding activity. Treatment of nuclear factors with proteinase K or incubation at 68° C. and 100° C. resulted in the loss of binding activity to EN-1, whereas RNaseI treatment did not influence the binding of proteins to DNA, indicating the proteinaceous nature of DNA binding factors. To determine the specificity of binding of the EN-1 element to nuclear proteins, a mixture of HhaI and Sau3A digested fragments from cloning vector pGEM3 were added to the binding assay mix. A 200 fold molar excess of pGEM3 fragments did not affect the formation of DNA/protein complex, whereas addition of 5 to 10 fold excess of unlabeled EN-1 DNA dramatically reduced the formation of complexes, indicating that the EN-1 element specifically competes for binding of the nuclear protein. Addition of an excess of unlabeled DNA fragment representing nucleotides −108 to +45 did not compete with labeled EN-1 element or vice versa, suggesting that binding activities of the −108 to +45 DNA fragment and the EN-1 DNA fragment are specific and distinct from one another.

5. Identification of Specific DNA Sequences that Interact with Nuclear Protein Factors To further confirm the specificity of binding and to define the specific region of DNA interacting with protein, DNAse I foot printing assays were performed utilizing the EN-1 DNA fragment. It was determined that nuclear factors protect a 35 base pair region of the promoter covering −757 bp to −722 bp from DNaseI action. To further confirm that DNA protection resulted from the binding-of proteins to this specific region, two complementary oligonucleotides (60 mers) containing this region were synthesized, annealed, purified by polyacrylamide gel chromatography and used for protein binding studies. The synthetic fragment of DNA showed a specific interaction with nuclear factors from cells adapted to 428 mM salt. These observations confirmed that the EN-1 sequence between nucleotides −757 to −722 is specifically interacting with nuclear factors isolated from cells and tissues that are actively expressing the osmotin transcript. Furthermore, methylation interference studies indicated that protein is not interacting with nucleotide G or C residues, because neither G nor C residues were protected.

GENERAL DISCUSSION

Gene Structure

Osmotin is encoded in *Nicotiana tabacum* by a pair of genes, each derived from one of the parental species, *N. sylvestris* and *N. tomentosiformis*. The promoter utilized here is from the *N. tabacum* gene derived from the *N. sylvestris* parent. The intronless osmotin gene has two putative transcription start sites (0 and −4). Both S1 nuclease and primer extension analyses indicated that transcripts are initiated from both sites.

Transcription Activation:

The nuclear run-on transcription assays indicate that by 6 hours after addition of 100 mM ABA, osmotin mRNA transcription rates have increased significantly in cell suspension cultures. Transcription of the wound-inducible DAHP synthase gene also increases by this treatment, potentially indicating that, similar to the situation with the potato proteinase inhibitor II gene, some molecular wound responses are mediated through ABA. However, for osmotin, the wound response is mostly reversible by 2,5-norbornadiene, indicating that the osmotin wound response is mediated through ethylene.

Inducibility of GUS, activity by ABA in R-1 progeny of three independent transgenic plants and a log-linear response of GUS activity to ABA concentration clearly indicate that the osmotin promoter is regulated by this plant hormone. The decrease in GUS activity during the developmental aging indicates that this gene is less response to exogenously applied ABA in more mature tissues. This result agrees with northern data of ABA-treated plants at different stages of maturity.

The observation that ABA inducibility depends on the growth stage of the plant seedlings helps to explain an anomaly observed in cultured cells. Namely, unadapted cells experience a maximum endogenous level of ABA (0.8 nmol/g fresh weight) equal to NaCl-adapted cells (see, Singh et al., *Proc. Natl. Acad. Sci. USA,* 84, 739–743 (1987)), yet the adapted cells accumulate much more osmotin mRNA. See, Singh et al., *Plant Physiol,* 90, 1096–1101 (1989). The difference in accumulation may be explained by the difference in the stage of the growth cycle where the peak level occurs. In unadapted cells, the peak occurs after the onset of logarithmic growth, whereas in adapted cells, the peak occurs prior to logarithmic growth. If the growth curve of seedlings (FIG. 3C) can be equated to the growth curve of cell suspension cultures, it becomes apparent that a dose of ABA prior to or at the onset of logarithmic growth results in an increased rate of transcription and high levels of mRNA accumulation, but an ABA dose at a later stage when the osmotin gene is much less responsive does not lead to osmotin mRNA accumulation.

Since NBD did not reverse the induction of GUS enzyme activity following ABA treatment, it is most likely that ABA does not induce ethylene synthesis which in turn could increase promoter activity. Apparently the transduction pathways for ABA and ethylene induction of the osmotin gene do not completely overlap, i.e. these pathways can operate independent of each other, at least in the tissues studied.

By introducing a chimeric gene fusion of the osmotin promoter and β-glucuronidase into tobacco by Agrobacterium-mediated transformation, a very specific pattern of temporal and spatial regulation of the osmotin promoter during normal plant development and after adaptation to NaCl has been demonstrated. It has been discovered that the osmotin promoter has a very high natural level of activity in mature pollen grains during anther dehiscence and in pericarp tissue at the final, desiccating stages of fruit development. GUS activity was rapidly lost after pollen germination. The osmotin promoter thus appears to be unique among active pollen promoters described to date in that it is active only in dehydrated pollen. The osmotin promoter was also active in corolla tissue at the onset of senescence. Adaptation of plants to NaCl highly stimulated osmotin promoter activity in epidermal and cortex parenchyma cells in the root elongation zone; in epidermis and xylem parenchyma cells in stem internodes; and in epidermis, mesophyll, and xylem parenchyma cells in developed leaves.

The results of DNase I foot printing analysis and the gel retardation assay demonstrate that the osmotin promoter contains at least two regions that showed distinct DNA/protein interactions. The abundance of DNA binding protein increased in response to ABA and ethylene treatment and also during the adaptation of cells to salt. These results suggest that an increase in DNA binding protein factors in response to the treatments of ABA, salt and ethylene can lead to the activation of the osmotin gene. One of the regions (nucleotides −108 to +45) that interacts with protein is close to the TATA box and the other region is farther away (nucleotides −762 to −642). The EN-1 element (nucleotides −762 to −642) that interacts with nuclear factors is present in a region of the promoter that is associated with maximal expression of the GUS reporter gene in transient expression studies, indicating that this sequence may act as an enhancer-like element. A 35 bp fragment protected from DNaseI action contains the sequence (TGTACTTCT) which shares 70% identity with the 10 bp (TCATCTTCTT) motif that is highly conserved among several stress-inducible genes.

Transient expression studies indicated that regions of the promoter providing for basal expression and ABA responsiveness of the reporter gene are also sufficient for the induction of reporter gene expression by ethylene, wounding, salt and desiccation. These observations confirm that the DNA fragment containing the osmotin promoter is able to activate transcription of the reporter gene in response to several inducers, whereas sequences further upstream show a quantitative enhancement in transcription.

All publications and U.S. patent applications cited herein are hereby incorporated by reference, each in its entirety, as if each had been individually incorporated by reference.

While the invention has been illustrated and described in detail in the foregoing description, the same is to be considered as illustrative and not restrictive in character, it being understood that only the preferred embodiments have been described and that all changes and modifications that come within the spirit of the invention are desired to be protected.

TABLE 1

| Sequence | Position |
|---|---|
| GTCGACTTTTGTATCAGTTGATGTTCTGGTAGTATTACACTAGACTTAGTTTCGTAACTGATTGTTTTATAAATTTCCGTAACGTTCAAATATGTCCT | -1900 |
| TACCGTCACATAGTTGGTCTATATATTTTTCTTTATATCCCTTTTGAAATAGAATCCATCCAAATTATTTAGCTCTCCGTTAATTATACTAAATGTATGACAAACACTA | -1800 |
| TTTCCTTTATTCAGTACTTTTTTTTCTTTATCAATTAACTTGACAAATCCTGTAATTTCATGAATTTACTATTACAGGCCCCACAGTTCCTTC | -1700 |
| CTGACCTGAAGGAGATGAAAATTATCGGAGAAATTTCTCGGTGGTGTTAATTGGCGTAAGTAGAATGATTATTCAAATTTGAAGATCTGTTCT | -1600 |
| TTCAGATCTGAAGCTCCACAGTGAACACTAGAGCCTTCTCCGGTGTGAAGGTTTTGCTCTACCTTCACCAAATTAACACCACAAATTCTTCGACAAT | -1500 |
| TTTATCTCCTTCTTTCAGAAGAAGGCACCGAAATGAGGAAGGCAAACCGGATATGTGAGGAAATGAAAACGGAAAAAGATAAGAAAAAATTCTTAGGAATCCACCGTCAAATTGGTAA | -1400 |
| CGAAAATGGAAGCACCATATGGTAAGGACATATATGAACCAACTATGTGTTTTGTAATACACTTTAATACACCTTTAATATGGAAAAGAGACTAATGAGTTGGGTGGATTCATTTTAA | -1300 |
| GGTAATTAACAAAGGGTTGGTCTTTATATAATTGTCTCCAATTCGTATATTGTTCATTTAATCTGCCAAAATGTTCCATAAATCTCCTTTAATTTGTATAATCATAGTTCTTCAGAGATTTTCTTCTTAAACAA | -1200 |
| AACCTATAAGGGGTTGGTCTTTATATATTGTCTCTTATTATCTACTTTATTAAGTTGTCACAAATTTTGTTAATACATAAGCCATATTGAGCTCGGACCTATAGTCTTCAGAGATTCTTCAGAGATTCTAAACAA | -1100 |
| ATTTCACAGAATTTATGTTAATGTTAATCTTCACTTTATTGTTCACAAATTGTCACTGATTAGCATCATGATGATTTTGTCTAGTTTATTGTGTTCTTC | -1000 |
| TCTGCGCTTATTCTACAATATCCAGAATAACGATATCTAATTAAATCAAGAGTTCATTCAATAAGTCTGTATAATTTTCTGTGTTCTTC | -900 |
| TATGTTGGTGGGACAATATCATCTATATATAAAATTAAATCAGGATTTCAGTATGAAATCCAATAAAATTATAAGTAACCAGAAAAAATTTATGATCGGTGCAAA | -800 |
| CTCCATAAAAAATTCCGAAGTACAAAATGTGAAGTTCAAAATGTCTAATAAACTGTCAATAAAACTGTCAATAAAACTGTCAATTTCTGAAT | -700 |
| ATTGTTTGAGTTTTATTTTCAGATAATGCTTTTAATAATGCTTTACATATGGCTATCTGCCAAAAAGTGCTATCTGCCAAAAAGTGCTATCTGTCAATTTCTGAAT | -600 |
| TAAAAATGCTATAGATAAAAGAAAGCAAGAAATGACTAAAAGATATTGTTAAAGCGCCGCTCTATGTTACAGAGATTATAGGTCAGCATTCTGAGATATCCGTT | -500 |
| AAATGACTTCTATATTCATAAATAATTTATGATTAATATATTTATGATCCATAGTACAAAAGCCCGCTATAATTCCCATATCCCTATATAAACCACTAACAATTGTCACTATGCTT | -400 |
| TATTAGTGAAATGTTAATGATTAATATGATCCTAGATATATTGATACCTATCAGCCCATTCCTCTCCTTGCCTTGGTGACTTATACTTATGCTGCCA | -300 |
| CAACCCAACTTGTTAAAATGTCCAACAACatgggcaacttgagatctctttgtttcttcctcctgactatacttatgctgcca | -100 |
| | -0 |
|   M  G  N  L  R  S  S  P  V  P  F  F  L  L  A  L  V  T  Y  T  Y  A  A  T | 100 |
| ctatcgagtgcgaaccaactgcaaacaccgttggcgcgttgacaccatggcggtggcggtggctgacccgcatcgaagccaactggggatcaa | |
| I  E  V  R  N  N  C  F  Y  T  V  H  A  A  S  T  P  I  G  G  R  R  L  D  R  G  Q  I  W  V  I  H | 200 |
| tgcgccacagagtactaaaatgcgaaatggggccgtgtagggggccgtactaattgaactttcaatgctgtgtagggggttgtccaaaccgttgctgtgtga | |
| A  P  R  G  T  K  M  A  R  V  W  Q  R  T  H  C  H  F  H  A  A  G  R  G  T  C  Q  T  G  D  C  G  G | 300 |
| gtcctcagtgccgaactcagttggcgccgactaaccctggctgaatacgttggccaattcagtgtgtagttagatttctggaacattcttagttg | |
| V  L  Q  C  T  G  W  G  K  P  P  N  T  L  A  E  Y  A  L  D  Q  F  S  G  L  D  F  W  D  I  S  L  V  D | 400 |
| atggatcaacacttccgatgacttttggccccgactaaccctggtggaggaaatgctagcaattaattgacggcactataaacggcgaatgcccg | |
| G  F  N  P  M  T  F  A  P  T  H  P  S  G  G  K  C  T  A  H  I  H  G  E  C  P  R | 500 |
| Cgaacttaggggtccccgatgataatacccttgctacattgctgacacaagccttgtgtcctacattttca | |
| E  L  R  V  P  G  C  N  H  P  C  T  T  F  G  G  Q  Q  Y  C  C  T  Q  R  P  C  G  G  S  T  H  Y  R  V  I | 600 |
| aaattttcaacaaagatgcaagctccaccaatgactcacaccagatgatcctacctagcactttactctgcccgtgtagtagcaattataggta | |
| K  F  F  K  Q  R  C  F  D  A  Y  S  Y  P  Q  D  D  P  T  S  T  F  T  C  P  G  G  S  T  H  Y  R  V  I | 700 |
| tcttttgccttaaggtcaagtccaaccaatttccctttgaaatgcctgaagtgagtgagtAGTGGCTATTTCTAATAAGATCAC* | |
| F  C  P  H  G  Q  A  H  P  N  F  P  L  E  M  P  G  S  D  E  V  A  K  * | 800 |
| CTTTGTCAAATATATCTATCCAACACTAGTAAGACAATCTATTGTTGACTCGTCTTTGTTGAAGTGATCAAGTCATGATCTTT | 900 |
| GCTGTAATAAACCTAAGACCTGAATAAGAGTCACATATGTATTTTGTCCTTGAATCAATAATGCATTTGAATTATATCGTTTTATATTGTT | 1000 |
| TTTCTTTTGAAGTTTTAGTAAAGTCTTAAGCTT | 1033 |

TABLE 1-continued
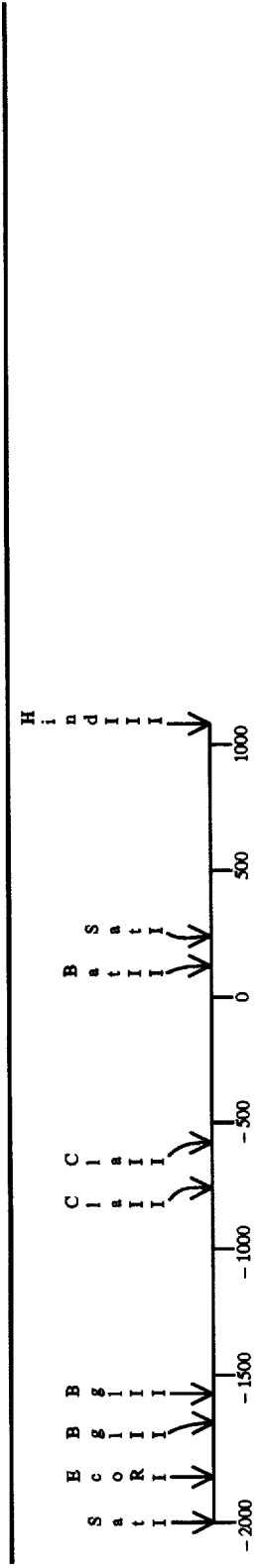

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3033 bases
        ( B ) TYPE: Nucleotide/Amino Acid
        ( C ) STRANDEDNESS: Double
        ( D ) TOPOLOGY: Linear ( i i ) MOLECULE TYPE: Genomic DNA ( x i ) SEQUENCE DESCRIPTION: SEQ ID NO:1:

```
GTCGACTTTT  GTATCAGTTG  ATGTTCTGGT  AGTATTACAC  TAGACTTAGT        50
TTCGTAACTG  ATTGTTTTAT  AAATTTTCCG  GTAACGTCCA  AATATGTCCT       100
TACCGTCACA  TAGTTGGTCT  ATATATCCCT  TTTTGAAATA  GAATCCATCC       150
AAATTATTTA  GCTCTTCCGT  TAATTATACT  AAAATGTATG  ACAAACACTA       200
TTTCCTTTTT  ATTCAGTACT  TTTTTTTCTT  TATCAATTTA  ACTTGACAAA       250
ACTCATGAAT  TCCTGTTAAT  TTTACTATTA  CAGGCCCAC   AGGTTCCTTC       300
CTGACCTGAA  GGAGATGAAA  ATTATCGGAG  AAATTTTTC   GGTGGTGTTA       350
ATTGGGTGAA  GGTAGGATAT  GATTATTCAA  ATTTTGAAGA  TCTTGTTCCT       400
TTCAGATCTG  AAGCTCCACA  GTGAACAACT  CCTTCAAAAT  CTGAATAATT       450
ATATCCTACC  TTCACCAAAT  TAACACCACC  AAAAAAATTT  CTCCGACAAT       500
TTTTATCTCC  TTCTTTTCAG  AAGAACTAGA  GCCTTCTCGG  TTGGAAGGTT       550
TTGGTGGTGC  AAGTTTGATT  TTTAGGAATA  AAATCACGTC  AAATTGGTAA       600
CGAAAATGGA  GAAGGCACCG  GAAATGGAGG  AAACCGGATA  TGGGAGAATG       650
AAAAAGGGAA  AAAAAGATAA  GAAAAGAAAA  AAGAAGAAAG  AAAAGAGAAA       700
GGTAAAGAAA  AAAAGTACTA  ATAAAAAGTA  GATAGTGTTT  GTAATACACT       750
TTAATACAAT  TAAAGAAAGA  GCTAATTAGT  TTGGGTGGAT  TCATTTTTAA       800
AAAGGGCAAC  TATGTGACGG  TAAGGACATA  TATGGACCAA  CTATGTGTAT       850
GGTAAGGGCA  TATATGGACC  AATTATGTGA  CGGTACGAGT  ATATATGAGC       900
TAAAGTATTA  ACAAAGGGTA  AATGTGCTCA  ATTTCGTATA  TTACAAAGCC       950
ATATTTGGAC  CTTTTTCCGT  AAATTTTATG  TAGATTTAGA  AAAAAGCAAC      1000
AACCTATAAG  GGGTTGGTCT  TTAAATATTG  TCTTCATTTT  TTAATGTACT      1050
TAAAGAATGA  GCTCTGGACC  TATATAGTTC  TTCAGAGATT  TTTCTATTGG      1100
ATCGCTAGAA  TTTATGTTAT  ATTTATTCTA  CTTTTATTGT  TAAGTGTTCA      1150
CAAATTTTAT  TCGATTAGCA  TGATTTGTG   CTAGTTTTAT  TGTTAAACAA      1200
ATTTCACAGA  ATCGGCGTAA  CTTTATTTTA  TCTGCAATCG  ATGTACTTCT      1250
TAAATTGTTC  ATTAAATCTA  CCTGACTGGT  ATAATTTTTC  TGTGTTCTTC      1300
TCTGCGCTTA  TTCTACATCC  AGAATAACGA  TATCTAATTA  ATGAGCTGCT      1350
ATATAAATCG  ATGTAATAGT  TCTCAAAAAG  AAAATGAAGG  AAGAAAAAAC      1400
TATGTGGTGG  GACAATATAA  CATCATCTAT  ATATAAAAAT  TAAAGTGAAA      1450
TCCAGGATTT  CAGTATTAAA  ACTACAGGAA  AAATTTATGA  TCGGTGCAAA      1500
```

-continued

| | |
|---|---|
| CTCCATAAAA AATTTCGGAA GTACAAAATG TGGAGTTCAA ACTGATAAAC | 1550 |
| AAACTCTAAT AAATTTCTTA TAATTTTTTT ATATTTTGT GACGAATATT | 1600 |
| ATTGTTTGAG TTTTATTTTC ACATTAAAAA CTAAATATTG AATAGCTTTA | 1650 |
| AAATGATGGC TATCTGCCAA AAAGTGGCTA TCTGTCAATT TCTTGCGAAT | 1700 |
| TAAAAAATGG TATAGATAAA AGAAAGCAAG AAATTGACTA AAGAGATAT | 1750 |
| TGTTACAAGT GTCACGTTAC AGAGATTATA GGTCAGCGTT ATTACCAAAT | 1800 |
| AAATTGACTT CTATATTCAT AAAATAATTA ATTATTAGGC GGCTCTTATG | 1850 |
| TTTAAGCGCC GCCTCCATCT TTGCCAAAGC ATCCTTGAGA TATATCCGTT | 1900 |
| TATTAGTCAA ATGTTAATAA ATATTTATGA TTAATATCCA TAGTACGAAA | 1950 |
| AGCCGCCATT CCCCTATATA AACCACTAAA CAATTTGTCA CTATATCCAA | 2000 |
| CAACCCAACT TGTTAAAAAA AATGTCCAAC AAC ATG GGC AAC TTG | 2045 |
|    Met Gly Asn Leu | |
|    1 | |

| | |
|---|---|
| AGA TCT TCT TTT GTT TTC TTC CTC CTT GCC TTG GTG ACT TAT<br>Arg Ser Ser Phe Val Phe Phe Leu Leu Ala Leu Val Thr Tyr<br>5          10          15 | 2087 |
| ACT TAT GCT GCC ACT ATC GAG GTC CGA AAC AAC TGT CCG TAC<br>Thr Tyr Ala Ala Thr Ile Glu Val Arg Asn Asn Cys Pro Tyr<br>20         25          30 | 2129 |
| ACC GTT TGG GCG GCG TCG ACA CCC ATA GGC GGT GGC CGG CGT<br>Thr Val Trp Ala Ala Ser Thr Pro Ile Gly Gly Gly Arg Arg<br>35         40          45 | 2171 |
| CTC GAT CGA GGC CAA ACT TGG GTG ATC AAT GCG CCA CGA GGT<br>Leu Asp Arg Gly Gln Thr Trp Val Ile Asn Ala Pro Arg Gly<br>50         55          60 | 2213 |
| ACT AAA ATG GCA CGT GTA TGG GGC CGT ACT AAT TGT AAC TTC<br>Thr Lys Met Ala Arg Val Trp Gly Arg Thr Asn Cys Asn Phe<br>65         70 | 2255 |
| AAT GCT GCT GGT AGG GGT ACG TGC CAA ACC GGT GAC TGT GGT<br>Asn Ala Ala Gly Arg Gly Thr Cys Gln Thr Gly Asp Cys Gly<br>75         80          85 | 2297 |
| GGA GTC CTA CAG TGC ACC GGG TGG GGT AAA CCA CCA AAC ACC<br>Gly Val Leu Gln Cys Thr Gly Trp Gly Lys Pro Pro Asn Thr<br>90         95         100 | 2339 |
| TTG GCT GAA TAC GCT TTG GAC CAA TTC AGT GGT TTA GAT TTC<br>Leu Ala Glu Tyr Ala Leu Asp Gln Phe Ser Gly Leu Asp Phe<br>105       110        115 | 2381 |
| TGG GAC ATT TCT TTA GTT GAT GGA TTC AAC ATT CCG ATG ACT<br>Trp Asp Ile Ser Leu Val Asp Gly Phe Asn Ile Pro Met Thr<br>120       125        130 | 2423 |
| TTC GCC CCG ACT AAC CCT AGT GGA GGG AAA TGC CAT GCA ATT<br>Phe Ala Pro Thr Asn Pro Ser Gly Gly Lys Cys His Ala Ile<br>135       140 | 2465 |
| CAT TGT ACG GCT AAT ATA AAC GGC GAA TGT CCC CGC GAA CTT<br>His Cys Thr Ala Asn Ile Asn Gly Glu Cys Pro Arg Glu Leu<br>145       150        155 | 2507 |
| AGG GTT CCC GGA GGA TGT AAT AAC CCT TGT ACT ACA TTC GGA<br>Arg Val Pro Gly Gly Cys Asn Asn Pro Cys Thr Thr Phe Gly<br>160       165        170 | 2549 |
| GGA CAA CAA TAT TGT TGC ACA CAA GGA CCT TGT GGT CCT ACA<br>Gly Gln Gln Tyr Cys Cys Thr Gln Gly Pro Cys Gly Pro Thr<br>175       180        185 | 2591 |
| TTT TTC TCA AAA TTT TTC AAA CAA AGA TGC CCT GAT GCC TAT<br>Phe Phe Ser Lys Phe Phe Lys Gln Arg Cys Pro Asp Ala Tyr<br>190       195        200 | 2633 |

-continued

| AGC | TAC | CCA | CAA | GAT | GAT | CCT | ACT | AGC | ACT | TTT | ACT | TGC | CCT | 2675 |
| Ser | Tyr | Pro | Gln | Asp | Asp | Pro | Thr | Ser | Thr | Phe | Thr | Cys | Pro | |
| | | | | 205 | | | | | 210 | | | | | |

| GGT | GGT | AGT | ACA | AAT | TAT | AGG | GTT | ATC | TTT | TGT | CCT | AAT | GGT | 2717 |
| Gly | Gly | Ser | Thr | Asn | Tyr | Arg | Val | Ile | Phe | Cys | Pro | Asn | Gly | |
| 215 | | | | | 220 | | | | | 225 | | | | |

| CAA | GCT | CAC | CCA | AAT | TTT | CCC | TTG | GAA | ATG | CCT | GGA | AGT | GAT | 2759 |
| Gln | Ala | His | Pro | Asn | Phe | Pro | Leu | Glu | Met | Pro | Gly | Ser | Asp | |
| | | 230 | | | | 235 | | | | | 240 | | | |

| GAA | GTG | GCT | AAG | TAG | AGTGGCTATT | TCTGTAATAA | GATCACCTTT | | | | | | | 2804 |
| Glu | Val | Ala | Lys | | | | | | | | | | | |
| | | | 245 | | | | | | | | | | | |

TGGTCAAATT ATTCTATCGA CACGTTAGTA AGACAATCTA TTTGACTCGT     2854

TTTTATAGTT ACGTACTTTG TTTGAAGTGA TCAAGTCATG ATCTTTGCTG     2904

TAATAAACCT AAGACCTGAA TAAGAGTCAC ATATGTATTT TTGTCTTGAT     2954

GTTATATAGA TCAATAATGC ATTTGGATTA TCGTTTTTAT ATTGTTTTTC     3004

TTTTGAAGTT TTAGTAAAGT CTTAAGCTT                            3033

( 2 ) INFORMATION FOR SEQ ID NO:2:

( i ) SEQUENCE CHARACTERISTICS:
        ( A ) LENGTH: 2051 bases
        ( B ) TYPE: Nucleotide/Amino Acid
        ( C ) STRANDEDNESS: Double
        ( D ) TOPOLOGY: Linear ( i i ) MOLECULE TYPE: Genomic DNA ( x i ) SEQUENCE DESCRIPTION: SEQ ID NO:2:

GTCGACTTTT GTATCAGTTG ATGTTCTGGT AGTATTACAC TAGACTTAGT     50

TTCGTAACTG ATTGTTTTAT AAATTTTCCG GTAACGTCCA AATATGTCCT    100

TACCGTCACA TAGTTGGTCT ATATATCCCT TTTTGAAATA GAATCCATCC    150

AAATTATTTA GCTCTTCCGT TAATTATACT AAAATGTATG ACAAACACTA    200

TTTCCTTTTT ATTCAGTACT TTTTTTTCTT TATCAATTTA ACTTGACAAA    250

ACTCATGAAT TCCTGTTAAT TTTACTATTA CAGGCCCCAC AGGTTCCTTC    300

CTGACCTGAA GGAGATGAAA ATTATCGGAG AAATTTTTTC GGTGGTGTTA    350

ATTGGGTGAA GGTAGGATAT GATTATTCAA ATTTTGAAGA TCTTGTTCCT    400

TTCAGATCTG AAGCTCCACA GTGAACAACT CCTTCAAAAT CTGAATAATT    450

ATATCCTACC TTCACCAAAT TAACACCACC AAAAAAATTT CTCCGACAAT    500

TTTTATCTCC TTCTTTTCAG AAGAACTAGA GCCTTCTCGG TTGGAAGGTT    550

TTGGTGGTGC AAGTTTGATT TTTAGGAATA AAATCACGTC AAATTGGTAA    600

CGAAAATGGA GAAGGCACCG GAAATGGAGG AAACCGGATA TGGGAGAATG    650

AAAAAGGGAA AAAAGATAA GAAAGAAAA AAGAAGAAAG AAAAGAGAAA    700

GGTAAAGAAA AAAAGTACTA ATAAAAAGTA GATAGTGTTT GTAATACACT    750

TTAATACAAT TAAAGAAAGA GCTAATTAGT TTGGGTGGAT TCATTTTTAA    800

AAAGGGCAAC TATGTGACGG TAAGGACATA TATGGACCAA CTATGTGTAT    850

GGTAAGGGCA TATATGGACC AATTATGTGA CGGTACGAGT ATATATGAGC    900

TAAAGTATTA ACAAAGGGTA AATGTGCTCA ATTTCGTATA TTACAAAGCC    950

ATATTTGGAC CTTTTTCCGT AAATTTTATG TAGATTTAGA AAAAAGCAAC    1000

AACCTATAAG GGGTTGGTCT TTAAATATTG TCTTCATTTT TTAATGTACT    1050

| | | | | |
|---|---|---|---|---|
| TAAAGAATGA | GCTCTGGACC | TATATAGTTC | TTCAGAGATT | TTTCTATTGG | 1100
| ATCGCTAGAA | TTTATGTTAT | ATTTATTCTA | CTTTATTGT | TAAGTGTTCA | 1150
| CAAATTTTAT | TCGATTAGCA | TGATTTGTG | CTAGTTTAT | TGTTAAACAA | 1200
| ATTTCACAGA | ATCGGCGTAA | CTTTATTTA | TCTGCAATCG | ATGTACTTCT | 1250
| TAAATTGTTC | ATTAAATCTA | CCTGACTGGT | ATAATTTTC | TGTGTTCTTC | 1300
| TCTGCGCTTA | TTCTACATCC | AGAATAACGA | TATCTAATTA | ATGAGCTGCT | 1350
| ATATAAATCG | ATGTAATAGT | TCTCAAAAAG | AAAATGAAGG | AAGAAAAAAC | 1400
| TATGTGGTGG | GACAATATAA | CATCATCTAT | ATATAAAAAT | TAAAGTGAAA | 1450
| TCCAGGATTT | CAGTATTAAA | ACTACAGGAA | AAATTTATGA | TCGGTGCAAA | 1500
| CTCCATAAAA | AATTTCGGAA | GTACAAAATG | TGGAGTTCAA | ACTGATAAAC | 1550
| AAACTCTAAT | AAATTTCTTA | TAATTTTTTT | ATATTTTGT | GACGAATATT | 1600
| ATTGTTTGAG | TTTTATTTTC | ACATTAAAAA | CTAAATATTG | AATAGCTTTA | 1650
| AAATGATGGC | TATCTGCCAA | AAAGTGGCTA | TCTGTCAATT | TCTTGCGAAT | 1700
| TAAAAAATGG | TATAGATAAA | AGAAAGCAAG | AAATTGACTA | AAAGAGATAT | 1750
| TGTTACAAGT | GTCACGTTAC | AGAGATTATA | GGTCAGCGTT | ATTACCAAAT | 1800
| AAATTGACTT | CTATATTCAT | AAAATAATTA | ATTATTAGGC | GGCTCTTATG | 1850
| TTTAAGCGCC | GCCTCCATCT | TTGCCAAAGC | ATCCTTGAGA | TATATCCGTT | 1900
| TATTAGTCAA | ATGTTAATAA | ATATTTATGA | TTAATATCCA | TAGTACGAAA | 1950
| AGCCGCCATT | CCCCTATATA | AACCACTAAA | CAATTTGTCA | CTATATCCAA | 2000
| CAACCCAACT | TGTTAAAAAA | AATGTCCAAC | AAC ATG GGC | AAC TTG | 2045
| AGA TCT | | | | | 2051

What is claimed is:

1. A method of inhibiting a pathogen in a plant, comprising the steps of:

(a) constructing a vector comprising an osmotin promoter and a foreign DNA sequence encoding a pathogen-inhibiting protein, wherein said osmotin promoter is operably linked to said foreign DNA sequence and includes:

(i) the nucleotide sequence 5' of the osmotin coding sequence extending to −248 of Table 1 (Seq. I.D. No. 1); or (ii) a nucleotide sequence which hybridizes to (i) and which promotes expression of an operably linked coding sequence under conditions of desiccation; and (b) introducing said vector into said plant to create a transformed plant, wherein the expression of said pathogen-inhibiting protein in said transformed plant is regulated by said osmotin promoter, wherein said pathogen is selected from the group consisting of a fungal pathogen, an insect pathogen, a nematode pathogen and a viral pathogen.

2. The method of claim 1, wherein said pathogen is a fungal pathogen.

3. The method of claim 2, wherein said structural gene encodes chitinase.

4. The method of claim 2, wherein said structural gene encodes (1-3)-β-glucanase.

5. The method of claim 2, wherein said structural gene encodes ribosome-inactivating protein.

6. The method of claim 2, wherein said structural gene encodes endopolygalacturonase.

7. The method of claim 1, wherein the osmotin promoter includes:

(c) the nucleotide sequence 5' of the osmotin coding sequence extending to −1630 of Table 1 (Seq. I.D. No. 1); or (d) a nucleotide sequence which hybridizes to (c) and which promotes expression of an operably linked coding sequence under conditions of desiccation.

8. The method of claim 7, wherein the osmotin promoter includes nucleotides 5' of the osmotin coding sequence extending no further than about −1196 in Table 1 (Seq. I.D. No. 1).

9. The method of claim 8, wherein the osmotin promoter includes nucleotides 5' of the osmotin coding sequence extending at least to about −496 but no further than about −1196 of Table 1 (Seq. I.D. No. 1).

10. A method of inhibiting a pathogen in a plant, comprising the steps of:

(a) providing a vector comprising an osmotin promoter and a foreign DNA sequence encoding a fungal pathogen-inhibiting protein, wherein said osmotin promoter is operably linked to said foreign DNA sequence and includes:

(i) the nucleotide sequence 5' of the osmotin coding sequence extending to −248 of Table 1 (Seq. I.D. No. 1); or (ii) a nucleotide sequence which hybridizes to (i) and which promotes expression of an operably linked coding sequence under conditions of dessication; and (b) introducing said vector into said plant to create a transformed plant, wherein the expression of said pathogen-inhibiting protein in said transformed plant is regulated by said osmotin promoter.

11. The method of claim 10, wherein said osmotin promoter is inducible under conditions of dessication, and wherein expression of said fungal pathogen-inhibiting protein is induced when said plant is subjected to conditions of dessication.

12. The method of claim 10, wherein the osmotin promoter includes:

(c) the nucleotide sequence 5' of the osmotin coding sequence extending to −1630 of Table 1 (Seq. I.D. No. 1); or (d) a nucleotide sequence which hybridizes to (c) and which promotes expression of an operably linked coding sequence under conditions of desiccation.

13. The method of claim 12, wherein the osmotin promoter includes nucleotides 5' of the osmotin coding sequence extending no further than about −1196 in Table 1 (Seq. I.D. No. 1).

14. The method of claim 13, wherein the osmotin promoter includes nucleotides 5' of the osmotin coding sequence extending at least to about −496 but no further than about −1196 of Table 1 (Seq. I.D. No. 1).

* * * * *

UNITED STATES PATENT AND TRADEMARK OFFICE
CERTIFICATE OF CORRECTION

PATENT NO. : 5,801,028
DATED : September 1, 1998
INVENTOR(S) : Ray Bressan et al.

It is certified that error appears in the above-identified patent and that said Letters Patent is hereby corrected as shown below:

In col. 1, directly after the title and before the REFERENCE TO RELATED APPLICATION section, please insert the following:
-- This invention was made with support under Grant No. DCB-9005216 from the National Science Foundation. The government has certain rights to the invention. --

Signed and Sealed this

Twenty-seventh Day of July, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO : 5,801,028

DATED : September 1, 1998

INVENTOR(S) : Ray Bressan et al.

It is certified that error appears in the above-identified patent and that said Letters Patent is hereby corrected as shown below:

col. 12, ln. 3 delete "Bql" and insert in lieu thereof —Bgl—.

In col's. 25-28, please delete Table 1 and insert in lieu thereof new Table 1 as it appears on the attached pages 2 and 3 of this request.

Signed and Sealed this

Second Day of January, 2001

*Attest:*

Q. TODD DICKINSON

*Attesting Officer*     *Commissioner of Patents and Trademarks*

TABLE 1

```
GTCGACTTTGTATCAGTTGATGTTCTCGGTAGTATTACACTAGACTTAGTTCGTAACTGATTGTTTTATAAATTTCCGTAACGTCCAAATATGTCCT    -1900
TACCGTCACATAGTGGTCTATATATCCCTTTTGAAATAGAATCCATCCAAATTATTTAGCTCTCCGTTAATTATACTAAAATTTACTAAACACTA      -1800
TTTCCTTTTTATTCAGTACTTTTTTTCTTATCAATTAACTGACAAACTCATGAATTCCTGTTAATTTACTATTACAGGCCCCACAGTTCCTTC        -1700
CTGACCCTGAAGGAGGAGATGAAAATTATCGGAGAAACTCCTTCAAGTCCCGTGGTGTTAATTGGGTGAAGGTAGGATATGATTATTCAAATTTGAAGATCTTGTTCCT -1600
TTCAGATCTGAAGCTCCACAGTGAACAACTCCTTCAAATCTGAATAATTATATCTACCTTCACCAAATTAACACCACCAAAAATTTCTCCGACAAT    -1500
TTTTATCTCCTTCTTTTCAGAAGAACTACCTCGTTGGAAGGCTTTTGGTGCAAGTTTGATTTTGATTCTTGCAAATAAAATCACGTCAAATTGGTAA   -1400
CGAAAATGGAGAAGGCACCGGAAATGGAGGAAACCGATATGGAGGAAACAATGAAAAGATAGAGTGTGTTGTAATACACTTAATACAATTAAGAAAGAAAAGATAGAGAGAAA -1300
GGTAAAGAAAAAAGTACTAATAAAAGTAGATAGTGTTTGTAATACACTTAATACAATTAAGAAAGAAAAGATAGAGAGAAA                    -1200
AAAGGCAACTATGTGACGGTAAGGCTAAATGTCTCAATTGCTATATTGTTCACGATATATCCCAATTAGTGACCTATATTGGGTGGATTCATTTTAA   -1100
TAAGTATTAACAAGGGTGGTCTTTAAATATTGTCTACTTTTATTGTTAAGTGTTCACAAATTTATTCGACCTATAGTTCTTGCTAGTTTTATTGTTAACAA  -1000
AACCTATAAGGGGTGGTCTTTAAATATTGTCTACTTTTATTGTTAAGTGTTCACAAATTTATTCGACCTATAGTTCTTGCTAGTTTTATTGTTAACAA    -900
ATCCTAGAATTTATGTCGGCGTAACTTTATTTATTCGCAATCGATATCTTAATTAATGAGCTGACTCCTTAAATTGTTCATTAAATCGATGTAATAGTTCTGTGTTCTTC -800
ATTTCACAGATCGGTATCCAGATATCATCAGATATCATCTATATATAACGATATCATCTATATATAAGTTCAGATAATAAATTTCTAATAAATTCTTATAAATTTTTATATTTTTGTGACGAATATT -700
TATGTGGTGGGACAATATATTCGGAAGTACAAAATTTCGGAAGTACAAAATGGAGTTCAAACTGATAAACTGATAAACTAAATATTATTAGGCGCTCTTAGTGTTTAAGCGCCATTCCCGTTAAGCCGCCATTCCCGTTAAGCCGCCATTCCC -600
CTCCATAAAAAATTTCGGAAGTACAAAATTTCGGAAGTACAAAATGGAGTTCAAACTGATAAACTAAATATTATTAGGCGCTCTTAGTGTTTAAGCGCC -500
ATTGTTTGAGTTTATTTCACATTAAAACATAAAAGAAGAAATGACTAAAAATTGACTAAAAATTGACTAAAAATTGACTAAAAATTGACTAAAAATTG -400
AAAATTGACTTCTATATTCATAAAATGTTAATAAAATATTTATGATTAATATCCATAGTACGAAAGCCGCCATTCCCTATATAAACCAATATCCGTT   -300
TATTAGTCAAATGTTAATAAAATATTTATGATTAATATCCATAGTACGAAAGCCGCCATTCCCTATATAAACCAATATCCGTT                   -200
CAACCCAACTTGTTAAAAAAATGTCAACAACatgggcaacttgagatcttcttttgttttcttcctcctgccttggtgacttatacttatgctgcca    -100
                                                                                                    0
ctatcgaggtcgaaacaactgtccgaaacttgtccgtacaccgttgggcggtcggcggcggtcggcggctcgatcgaggctcgcgaggcaaactgggtgatcaa  100

M  G  N  L  R  S  S  F  V  F  F  L  L  A  L  V  T  Y  T  Y  A  A  T
                      W  A  A  S  T  P  I  G  G  G  R  R  L  D  R  G  Q  T  W  V  I  N  200

I  E  V  R  N  N  C  P  Y  T  V
```

*To Table 1, Continued*

TABLE 1, CONTINUED

```
tgcgccacgaggtactaaaatggcacgtgtatgggccgtactaattgtaacttcaatgctgctggtagggtacgtgccaaccgtgactgtggtgga    300
 A  P  R  G  T  K  M  A  R  V  W  G  R  T  N  C  N  F  N  A  A  G  R  G  T  C  Q  T  G  D  C  G  G gtcctacagtgcaccgggtgggtaaaccacaccttggctgaatacgcttggacttagattctggacatttcttagttg                      400
 V  L  Q  C  T  G  W  G  K  P  P  N  T  L  A  E  Y  A  L  D  Q  F  S  G  L  D  F  W  D  I  S  L  V  D atggattcaacattccgatgactttcgccccgactaacccagtgcgagggaaatgcatgcaattcattgtacggctaatataaacggcgaatgtcccg  500
 G  F  N  I  P  M  T  F  A  P  T  N  P  S  G  G  K  C  H  A  I  H  C  T  A  N  I  N  G  E  C  P  R cgaacttagggttcccggagatgtaataaccctgtactacattcggaggacaacaatatattgttgcacacaaggaccttgtgtcctacattttctca  600
 E  L  R  V  P  G  G  C  N  N  P  C  T  T  F  G  G  Q  Q  Y  C  C  T  Q  R  P  C  G  P  T  F  F  S aaattttcaaacaaagatgccctgatgcctatagctcactactcacctttactgccctgtggtagtacaaattataggtta                    700
 K  F  F  K  Q  R  C  P  D  A  Y  S  Y  P  Q  D  D  P  T  S  T  F  T  C  P  G  G  S  T  N  Y  R  V  I tcttttgtcctaatggtcaagctcaaatttccctggaaatgcctggaagtgatgaagtagAGTGGCTATTTCTGTAATAAGATCAC               800
 F  C  P  N  G  Q  A  H  P  N  F  P  L  E  M  P  G  S  D  E  V  A  K CTTTTGGTCAAATTATTCTATCGACACGTTAGTAAGACAATCTATTGACTCGTTTTTGTTGAAGTGATCAAGTCATGATCTTT                 900
GCTGTAATAAACCTAAGACCTGAATAAGAGTCACATGTATTTTGTCTTGATGTTATATAGATCAATAATGCATTTGGATTATCGTTTTATATTGTT    1000
TTTCTTTGAAGTTTTAGTAAAGTCTTAAGCTT                                                                    1033
```